(12) United States Patent
Ngo et al.

(10) Patent No.: US 8,765,162 B2
(45) Date of Patent: *Jul. 1, 2014

(54) POLY(AMIDE) AND POLY(ESTER-AMIDE) POLYMERS AND DRUG DELIVERY PARTICLES AND COATINGS CONTAINING SAME

(75) Inventors: Michael Huy Ngo, San Jose, CA (US); Mikael O. Trollsas, San Jose, CA (US); Thierry Glauser, Redwood City, CA (US); Jinping Wan, San Jose, CA (US); Bozena Zofia Maslanka, Aptos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 527 days.

This patent is subject to a terminal disclaimer.

(21) Appl. No.: 12/165,173

(22) Filed: Jun. 30, 2008

(65) Prior Publication Data

US 2009/0324671 A1 Dec. 31, 2009

(51) Int. Cl.
*A61F 2/02* (2006.01)
(52) U.S. Cl.
USPC ............................ 424/423; 424/422; 528/310
(58) Field of Classification Search
USPC ................................. 528/310; 424/422, 423
See application file for complete search history.

(56) References Cited

U.S. PATENT DOCUMENTS

| | | | |
|---|---|---|---|
| 4,293,539 A | 10/1981 | Ludwig et al. | |
| 4,304,767 A | 12/1981 | Heller et al. | |
| 4,622,244 A | 11/1986 | Lapka et al. | |
| 4,800,882 A | 1/1989 | Gianturco | |
| 4,886,062 A | 12/1989 | Wiktor | |
| 4,897,268 A | 1/1990 | Tice et al. | |
| 4,954,298 A | 9/1990 | Yamamoto et al. | |
| 5,208,324 A | 5/1993 | Klaveness et al. | |
| 4,733,665 B1 | 1/1994 | Palmaz | |
| 5,383,928 A | 1/1995 | Scott et al. | |
| 5,419,760 A | 5/1995 | Narciso, Jr. | |
| 5,575,815 A | 11/1996 | Slepian et al. | |
| 5,581,387 A | 12/1996 | Cahill | |
| 5,607,475 A | 3/1997 | Cahalan et al. | |
| 5,646,160 A | 7/1997 | Morris et al. | |
| 5,725,568 A | 3/1998 | Hastings | |
| 5,782,908 A | 7/1998 | Cahalan et al. | |
| 5,843,156 A | 12/1998 | Slepian et al. | |
| 5,861,387 A | 1/1999 | Labrie et al. | |
| 5,874,165 A | 2/1999 | Drumheller | |
| 5,880,220 A * | 3/1999 | Warzelhan et al. | 525/424 |
| 5,891,192 A | 4/1999 | Murayama et al. | |
| 5,897,955 A | 4/1999 | Drumheller | |
| 5,914,182 A | 6/1999 | Drumheller | |
| 6,015,815 A | 1/2000 | Mollison | |
| 6,087,479 A | 7/2000 | Stamler et al. | |
| 6,174,539 B1 | 1/2001 | Stamler et al. | |
| 6,224,794 B1 | 5/2001 | Amsden et al. | |
| 6,290,729 B1 | 9/2001 | Siepian et al. | |
| 6,329,386 B1 | 12/2001 | Mollison | |
| 6,379,379 B1 | 4/2002 | Wang | |
| 6,379,382 B1 | 4/2002 | Yang | |
| 6,471,978 B1 | 10/2002 | Stamler et al. | |
| 6,497,729 B1 | 12/2002 | Moussy et al. | |
| 6,503,538 B1 | 1/2003 | Chu et al. | |
| 6,506,408 B1 | 1/2003 | Palasis | |
| 6,514,734 B1 | 2/2003 | Clapper et al. | |
| 6,528,093 B1 | 3/2003 | Kamei et al. | |
| 6,548,637 B1 | 4/2003 | Persons et al. | |
| 6,585,764 B2 | 7/2003 | Wright et al. | |
| 6,613,082 B2 | 9/2003 | Yang | |
| 6,613,084 B2 | 9/2003 | Yang | |
| 6,616,765 B1 | 9/2003 | Castro et al. | |
| 6,623,521 B2 | 9/2003 | Steinke et al. | |
| 6,652,575 B2 | 11/2003 | Wang | |
| 6,703,040 B2 | 3/2004 | Katsarava et al. | |
| 6,746,773 B2 | 6/2004 | Llanos et al. | |
| 6,767,637 B2 | 7/2004 | Park et al. | |
| 7,048,947 B2 | 5/2006 | Kamei et al. | |
| 7,056,591 B1 | 6/2006 | Pacetti et al. | |
| 7,060,299 B2 | 6/2006 | Alavattam et al. | |
| 7,166,680 B2 | 1/2007 | DesNoyer et al. | |
| 7,202,325 B2 | 4/2007 | Hossainy et al. | |
| 7,208,010 B2 | 4/2007 | Shanley et al. | |
| 7,220,816 B2 | 5/2007 | Pacetti et al. | |
| 7,247,313 B2 | 7/2007 | Roorda et al. | |
| 7,731,987 B2 * | 6/2010 | DesNoyer et al. | 424/423 |
| 7,910,152 B2 | 3/2011 | Kleiner et al. | |
| 8,323,676 B2 * | 12/2012 | Lim et al. | 424/423 |
| 2001/0027340 A1 | 10/2001 | Wright et al. | |
| 2003/0129130 A1 | 7/2003 | Guire et al. | |
| 2004/0033251 A1 | 2/2004 | Sparer et al. | |

(Continued)

FOREIGN PATENT DOCUMENTS

| | | |
|---|---|---|
| EP | 0 778 250 | 6/1996 |
| EP | 1 795 185 | 6/2007 |
| WO | WO 94/09010 | 4/1994 |
| WO | WO 2005/092406 | 10/2005 |
| WO | WO 2006/112932 | 10/2006 |
| WO | WO 2010/002584 | 1/2010 |

OTHER PUBLICATIONS

U.S. Appl. No. 10/816,072, filed Mar. 31, 2004, Dugan et al.
"*90Plus Particle Size Analyzer*" Brookhaven Instruments Corp. downloaded from www.bic.com/90Plus.html., Mar. 4, 2008, 6 pgs.
"*Available Particle Characterization Technologies*", downloaded from www.malvern.com/LabEng/support/technologies.htm., Mar. 5, 2008, 3 pgs.
"*Laser Light Scattering*", downloaded from www.ap-lab.com/light_scattering.htm, Mar. 5, 2008, 8 pgs.

(Continued)

Primary Examiner — Gregory Listvoyb
(74) Attorney, Agent, or Firm — Squire Sanders (US) LLP

(57) ABSTRACT

The current invention relates to poly(amide) and poly(ester-amide) polymers, coatings including the polymers, and narrow polydispersity drug delivery particles including the polymers.

15 Claims, 4 Drawing Sheets

(56) References Cited

U.S. PATENT DOCUMENTS

| | | |
|---|---|---|
| 2004/0106985 A1 | 6/2004 | Jang |
| 2004/0170685 A1 | 9/2004 | Carpenter et al. |
| 2004/0172121 A1 | 9/2004 | Eidenschink et al. |
| 2004/0172127 A1 | 9/2004 | Kantor |
| 2004/0228831 A1 | 11/2004 | Belinka et al. |
| 2004/0236415 A1 | 11/2004 | Thomas |
| 2005/0095267 A1 | 5/2005 | Campbell et al. |
| 2005/0106204 A1 | 5/2005 | Hossainy et al. |
| 2005/0112171 A1 | 5/2005 | Tang et al. |
| 2005/0137381 A1 | 6/2005 | Pacetti et al. |
| 2005/0147647 A1 | 7/2005 | Glauser et al. |
| 2005/0181015 A1 | 8/2005 | Zhong |
| 2005/0208091 A1 | 9/2005 | Pacetti |
| 2005/0208093 A1 | 9/2005 | Glauser et al. |
| 2005/0245637 A1 | 11/2005 | Tang et al. |
| 2005/0265960 A1 | 12/2005 | Pacetti et al. |
| 2005/0271700 A1 | 12/2005 | DesNoyer et al. |
| 2005/0288481 A1* | 12/2005 | DesNoyer et al. ............ 528/310 |
| 2006/0089485 A1 | 4/2006 | DesNoyer et al. |
| 2006/0093842 A1 | 5/2006 | DesNoyer et al. |
| 2006/0115513 A1 | 6/2006 | Hossainy |
| 2006/0142541 A1 | 6/2006 | Hossainy |
| 2006/0147412 A1 | 7/2006 | Hossainy et al. |
| 2006/0198870 A1 | 9/2006 | Mollison et al. |
| 2007/0003589 A1 | 1/2007 | Astafieva et al. |
| 2007/0280991 A1 | 12/2007 | Glauser et al. |
| 2007/0293941 A1 | 12/2007 | Gale et al. |
| 2008/0014236 A1 | 1/2008 | Pacetti et al. |
| 2008/0014241 A1* | 1/2008 | DesNoyer et al. ............ 424/423 |
| 2008/0145402 A1 | 6/2008 | Mollison et al. |
| 2009/0258028 A1 | 10/2009 | Glauser et al. |
| 2009/0324672 A1 | 12/2009 | Lim et al. |
| 2010/0047319 A1 | 2/2010 | Ngo et al. |
| 2011/0151104 A1 | 6/2011 | Kleiner et al. |
| 2011/0153004 A1 | 6/2011 | Kleiner et al. |
| 2011/0200660 A1 | 8/2011 | Kleiner et al. |

OTHER PUBLICATIONS

"*Microemulsion characterization using dynamic light scattering*", Zetasizer Nano application note, downloaded from www.malvern.co.uk, 3 pgs. no date.

"*Pigment Milling and Monitoring Particle Size Using Dynamic Light Scattering Techniques from Malvern Instruments*", downloaded from www.azom.com/details.asp?ArticleID=2724, Apr. 10, 2008, 5 pgs.

"*Taking the "suspense" out of Nanosuspension Specifications*", downloaded from www.pharmtech.findpharma.com/pharmtech/content/printContentPopup.jsp, Apr. 9, 2008, 3 pgs.

"*Toner size and shape characterization using FPIA-2100*", FPIA-2100 application note, downloaded from www.malvern.co.uk, 5 pgs. no date.

"*When Particle Size is Important*", Brookhaven Instruments corp. downloaded from www.bic.com/Particle_sizers_overview_.html, Mar. 5, 2008, 7 pgs.

Berkland et al., "*Controlling surface namo-structure using flow-limited field-injection electrostatic spraying (FFESS) of poly(D,L-lactide-co-glycolide)*", Biomaterials 25, pp. 5649-5658 (2004).

Berkland et al., "*Fabrication of PLG microspheres with precisely controlled and monodisperse size distributions*", J. of Controlled Release 73, pp. 59-74. (2001).

Berkland et al., "*Precise control of PLG microsphere size provides enhanced control of drug release rate*", J. of Controlled Release 82, pp. 137-147 (2002).

Berkland et al., "*Precission Polymer Microparticles for Controlled-Release Drug Delivery*", Am. Chem. Soc. pp. 197-213 (2004).

Bin Choy et al., "*Uniform Biodegradable Hydrogel Microspheres Fabricated by a Surfactant—Free Electric-Field-Assisted Method*", Macromol. Biosci. vol. 7, pp. 423-428 (2007).

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.

Costa et al., "Effect of uniform sized polymeric microspheres prepared by membrane emulsification technique on controlled release of anthracycline anti-cancer drugs", Desalination vol. 200, issues 1-3, pp. 498-500 (2006).

De Lezo et al., *Intracoronary Ultrasound Assessment of Directional Coronary Atherectomy: Immediate and Follow-Up Findings*, JACC vol. 21, No. 2, (1993) pp. 298-307.

Dubey et al., "*Factorial Effect of Process Parameters on Pharmaceutical Characteristics & Stability Study of PLGA Microspheres Containing Water-Soluble Drug*", downloaded from www.drugdeliverytech.com/cgi-bin/articles.cgi?Article=229, Mar. 9, 2008, 13 pgs.

Finsy et al., "*Particle Sizing by Photon Correlation Spectroscopy. Part II: Average values*", Particle and particle Systems Characterization vol. 8, issue 1-4, pp. 187-193, Abstract 1 pg. (2004).

Hanus et al., "*Conversion of intensity-averaged photon correlation spectroscopy measurements to number-averaged particle size distributions. 1. Theoretical development*", Langmuir vol. 15, No. 9, Abstract 1 pg. (1999).

Hua Ai et al., "*Biomedical applications of electrostatic layer-by-layer nano-assembly of polymers, enzymes, and nanoparticles*", Cell Biochem. and Biophysics, vol. 39, No. 1, Abstract 1 pg. (2003).

Kim et al., "*Drug Delivery, Contolled-release*" Office of Technology Management Univ. of Ill., 2 pgs. (2005-2006).

Kippax, "*Measuring particle size using modern laser diffraction techniques*", downloaded from www.analytica-world.com/articles/e/, Mar. 5, 2008, 4 pgs.

Kosvintsev et al., "*Liquid-Liquid Membrane Dispersion in a Stirred Cell with and without Controlled Shear*", Ind. Eng. Chem. Res. 44, pp. 9323-9330 Abstract only, 1 pg. (2005).

Lee et al., "*In-vivo biocompatibility evaluation of stents coated with a new biodegradable elastomeric and functional polymer*" Coron. Artery. Dis., 13(4): (2002) pp. 237-241.

Micropore Technologies *emulsions-particles-filtration*, Abstract, 1 pg. downloaded from www.micropore.co.UK, Mar. 19, 2008.

Moreno et al., *Macrophage Infiltration Predicts Restenosis After Coronary Intervention in Patients with Unstable Angina*, Circulation, vol. 94, No. 12, (1996) pp. 3098-3102.

Nakashima et al., "*Particle control of emulsion by membrane emulsification and its applications*", Advanced Drug Del. Rev. 45 pp. 47-56 (2000).

Oikawa et al., *Mechanisms of Acute Gain and Late Lumen Loss After Atherectomy in Different Preintervention Arterial Remodeling Patterns, The Am. J. of Cardilogy*, vol. 89, (2002) pp. 505-510.

Scully et al., *Effect of a heparan sulphate with high affinity for antithrombin III upon inactivation of thrombin and coagulator Factor Xa*, Biochem J. 262, (1989) pp. 651-658.

The knowledge database about lactose, Particle Size Distribution D10, D50 and D90, downloaded from www.lactose.com/particle_size/d10_d50_d90.html, Apr. 9, 2008, 2 pgs.

Virrnani et al., *Lessons From Sudden Coronary Death a Comprehensive Morphological Classification Scheme for Atherosclerotic Lesions*, Arterioscler Thromb Vasc Biol. (2000) pp. 1262-1275.

International Search Report for PCT/US2007/013327, filed May 6, 2007, mailed Nov. 30, 2007, 14 pgs.

UNOXOL™ Diol—The New Building Block for Coating, Dow Chem. Co. Product Information (2011) 1 pg.

* cited by examiner

POLY(AMIDE) AND POLY(ESTER-AMIDE) POLYMERS AND DRUG DELIVERY PARTICLES AND COATINGS CONTAINING SAME

FIELD

This invention relates to organic chemistry, polymer chemistry, physiology, material science and drug delivery.

BACKGROUND

Until the mid-1980s, the accepted treatment for atherosclerosis, i.e., narrowing of the coronary artery(ies) was coronary by-pass surgery. While effective and having evolved to a relatively high degree of safety for such an invasive procedure, by-pass surgery still involves serious potential complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, failed to satisfactorily ameliorate another problem, restenosis, the re-clogging of the treated artery.

The next improvement, advanced in the mid-1980s was use of a stent to hold the vessel walls apart after PTCA. This for all intents and purposes put an end to recoil but did not entirely resolve the issue of restenosis. That is, prior to the introduction of stents, restenosis occurred in from 30-50% of patients undergoing PTCA. Stenting reduced this to about 15-20%, much improved but still more than desirable.

In 2003, drug-eluting stents or DESs were introduced. The drugs initially employed with the DES were cytostatic compounds, compounds that curtailed the proliferation of cells that resulted in restenosis. The occurrence of restenosis was thereby reduced to about 5-7%, a relatively acceptable figure. Today, the DES is the default the industry standard to treatment of atherosclerosis and is rapidly gaining favor for treatment of stenoses of blood vessels other than coronary arteries such as peripheral angioplasty of the femoral artery.

One of the key criteria of DESs is selection of a polymer or blend of polymers to be used in a drug reservoir layer, a rate-controlling layer, a protective topcoat layer, etc. If a biostable polymer is selected, i.e., a polymer that does not significantly decompose in a patient's body, their chemical composition is often not of significant concern since they are not intended to break down and enter the patient's system. On the other hand, currently biodegradable polymers are preferred for many applications because their ability to decompose in a biological environment confers on them a number of desirable characteristics. For example, the fact that a polymer will biodegrade and can eventually be essentially completely eliminated from a patient's body can avoid the need to invasively remove a DES after its job is done. In addition, by judicious choice of biodegradable polymer, e.g., selecting one that bio-erodes by bulk erosion or one that bio-erodes by surface erosion, the properties of the polymer can be used as an added tool for the fine-tuning of the release rate of a drug.

Of course, if a polymer is going to degrade in a patient's body, it is imperative that it be biocompatible, that is, that its degradation products do no harm to the patient. This requires careful attention to the chemistry of the polymer and the properties of its degradation products. A great deal of work has gone into the effort to find suitable biodegradable polymers and one class of such polymers that is exhibiting particularly desirable properties in terms of biodegradation, biocompatibility, drug compatibility and, generally, the range of properties that can be engineered into the polymer by judicious selection their constitutional units is the poly(ester-amide) family of polymers.

As currently employed, however, poly(ester-amide)s tend generally to be rather soft and quite permeable to many if not most drugs, which limits their application in DESs to some extent. There is a need for polymers that are stronger, tougher and less permeable than those currently in use while still maintaining the other beneficial characteristics of the class.

Such polymers would have use in other areas of drug delivery including particles for drug delivery. Particles including a drug can be used for local drug delivery. Local drug delivery has advantages over systemic delivery. Specifically, by avoiding the gastrointestinal tract, the drug is not subject to the first pass metabolism in the liver, although it will still be subject to metabolism by enzymes that exist outside the gastrointestinal tract. In addition, by delivering the drug to the site where it is needed, there is a potential to obtain higher concentrations of drug at the site since systemic delivery to obtain the same local concentration may result in toxicity or adverse events. It is often preferred that polymers used to make drug delivery particles be biodegradable. This avoids the issue of removal which may not even be feasible for small particles.

The current invention provides polymers, poly(ester-amide) polymers and poly(amide) polymers, that are stronger, tougher and more compatible with active pharmaceutical ingredients than those currently in use while still maintaining the other beneficial characteristics of the class of poly(ester-amide)s. The polymers may be used for drug delivery coatings and drug delivery particles.

SUMMARY

The current invention relates to poly(amide) and poly(ester-amide) polymers, drug delivery coatings including the polymers, and drug delivery particles including the polymers.

Thus, in one aspect, the present invention relates to a polymer having the formula:

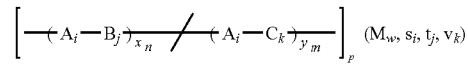

wherein
i is an integer from 1 to 10, inclusive;
j is an integer from 0 to 10, inclusive;
k is an integer from 0 to 15, inclusive;
$x_n$ is an integer from 0 to 100, inclusive;
$y_m$ is an integer from 0 to 150, inclusive;
p is an integer from 2 to about 4500;
$M_w$ is from about 10,000 to about 1,000,000 Da;
$s_i$ is a number from 0 to 0.5, inclusive;
$t_j$ is a number from 0 to 0.5, inclusive;
$v_k$ is a number from 0 to 0.5, inclusive;
with the proviso that $$\Sigma_i s_i + \Sigma_j t_j + \Sigma_k v_k = 1.0;$$

$$\Sigma_i s_i = \Sigma_j t_j + \Sigma_k v_k = 0.5;$$

$$\Sigma_i s_i > 0;$$

$$\Sigma_j t_j > 0 \text{ or } \Sigma_k v_k > 0;$$

each $A_i$ has the chemical structure:

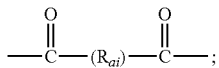

each $B_j$ has the chemical structure

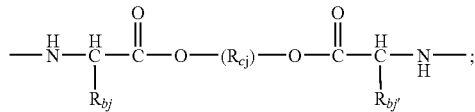

and
each $C_k$ has the chemical structure:

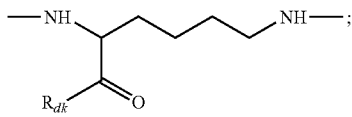

wherein:
each $R_{bj}$ and $R_{bj'}$ are independently selected from the group consisting of hydrogen and (1C-4C)alkyl, wherein:
the alkyl group is optionally substituted with a moiety selected from the group consisting of —OH, —SH, —SeH, —C(O)OH, —NHC(NH)NH$_2$,

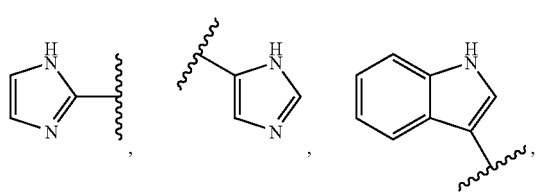

phenyl and

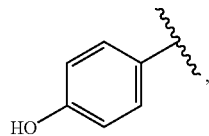

or
one or more of $R_{bj}$ and $R_{bj'}$ may form a bridge between the carbon to which it is attached and the adjacent nitrogen, the bridge comprising —CH$_2$CH$_2$CH$_2$—;
each $R_{ai}$ and each $R_{cj}$ are independently selected from the group consisting of (1C-12C)alkyl, (2C-12C)alkenyl, (3C-8C)cycloalkyl, —(CH$_2$CH$_2$O)$_q$CH$_2$CH$_2$— wherein q is an integer from 1 to 10, inclusive, and

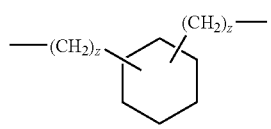

where z is 0, 1, or 2, wherein:
at least one $R_{ai}$ or at least one $R_{cj}$ is selected from the group consisting of

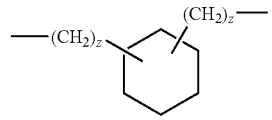

where z is 0, 1, or 2;
$R_{dk}$ is selected from the group consisting of a drug, a straight or branched chain polymer, a brush polymer, a paramagnetic moiety, a contrast agent, —H, —OH, —O(1C-20C)alkyl, —O(1C-20C)alkenyl and —O(CH$_2$CH$_2$O)$_w$CH$_2$CH$_2$OR$_{ek}$, wherein:
w is an integer from 1 to 600, inclusive;
$R_{ek}$ is selected from the group consisting of hydrogen, —C(O)CH=CH$_2$ and —C(O)C(CH$_3$)=CH$_2$; and,
each $R_{ai}$ corresponds to the $i^{th}$ $A_i$ group, each $R_{bj}$, $R_{bj'}$, and $R_{cj}$ corresponds to the $j^{th}$ $B_j$ group, and each $R_{dk}$ and optionally $R_{ek}$ correspond to the $k^{th}$ $C_k$ group.

In an aspect of this invention, each $R_{ai}$ and each $R_{cj}$ are independently selected from the group consisting of (1C-12C)alkyl, (1C-12C)alkenyl, and

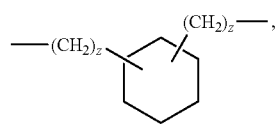

where z is 0, 1, or 2.
In an aspect of this invention, for each $B_j$, $R_{bj}$, and $R_{bj'}$ are the same.
In an aspect of this invention, for each $B_j$, the $R_{bj}$, and $R_{bj'}$ are selected from the group consisting of —CH$_3$, —CH$_2$CH(CH$_3$)$_2$, and

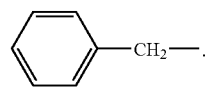

In an aspect of this invention, each $R_{cj}$ is selected from the group consisting of (1C-12C)alkyl, (1C-12C)alkenyl, —(CH$_2$CH$_2$O)$_q$CH$_2$CH$_2$— wherein q is an integer from 1 to 10, inclusive, and

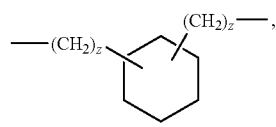

where z is 0, 1, or 2.
In an aspect of this invention, i≤2, j=2, and k=0;
each of $R_{a1}$ and $R_{a2}$ are independently selected from the group consisting of —(CH$_2$)$_6$—, —(CH$_2$)$_7$—, —(CH$_2$)$_8$—, —(CH$_2$)$_9$—, and —(CH$_2$)$_{10}$—;
each of $R_{b1}$, $R_{b1'}$, $R_{b2}$ and $R_{b2'}$ are the same, and are selected from the group consisting of —(CH$_2$)—(CH(CH$_3$)$_2$) and —CH$_3$;
$R_{c1}$ is selected from the group consisting of —(CH$_2$)$_4$—, —(CH$_2$)$_5$—, —(CH$_2$)$_6$—, —(CH$_2$)$_7$—, and —(CH$_2$)$_8$—;
and $R_{c2}$ is selected from the group consisting of

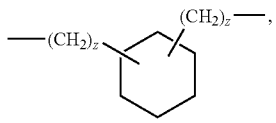

where z is 0, 1, or 2.

In an aspect of this invention, i≤2, j=2, and k=0;
each of $R_{a1}$ and $R_{a2}$ are independently selected from the group consisting of —(CH$_2$)$_6$—, —(CH$_2$)$_7$—, —(CH$_2$)$_8$—, —(CH$_2$)$_9$—, and —(CH$_2$)$_{10}$—;
each of $R_{b1}$, $R_{b1'}$, $R_{b2}$ and $R_{b2'}$ are the same, and are selected from the group consisting of —(CH$_2$)—(CH(CH$_3$)$_2$) and —CH$_3$;
$R_{c1}$ is selected from the group consisting of —(CH$_2$)$_4$—, —(CH$_2$)$_5$—, —(CH$_2$)$_6$—, —(CH$_2$)$_7$—, and —(CH$_2$)$_8$—; and
$R_{c2}$ is selected from the group consisting of

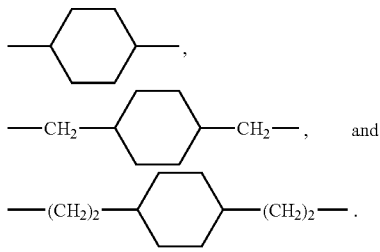

In an aspect of this invention, i=1, j=2, and k=0;
$R_{a1}$ is —(CH$_2$)$_8$—;
$R_{b1}$, $R_{b1'}$, $R_{b2}$ and $R_{b2'}$ are —(CH$_2$)—(CH(CH$_3$)$_2$);
$R_{c1}$ is —(CH$_2$)$_6$—;
$R_{c2}$ is selected from the group consisting of

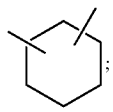

$s_1$=0.5; and $t_1$ is between 0.225 and 0.275, inclusive.
In an aspect of this invention, i=1, j=2, and k=0;
$R_{a1}$ is —(CH$_2$)$_8$—;
$R_{b1}$, $R_{b1'}$, $R_{b2}$ and $R_{b2'}$ are —(CH$_2$)—(CH(CH$_3$)$_2$);
$R_{c1}$ is —(CH$_2$)$_6$—;
$R_{c2}$ is

and
$s_1$=0.5; and $t_1$ is between 0.225 and 0.275, inclusive.
In an aspect of this invention, i=1, j=2, and k=0;
$R_{a1}$ is —(CH$_2$)$_8$—;
$R_{b1}$, $R_{b1'}$, $R_{b2}$ and $R_{b2'}$ are —(CH$_2$)—(CH(CH$_3$)$_2$);
$R_{c1}$ is —(CH$_2$)$_6$—;

$R_{c2}$ is selected from the group consisting of

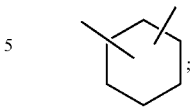

$s_1$=0.5; and $t_1$ is between 0.10 and 0.40, inclusive.
In an aspect of this invention, $R_{c2}$ is

In an aspect of this invention, i=1, j=2, and k=0;
$R_{a1}$ is —(CH$_2$)$_8$—;
$R_{b1}$, $R_{b1'}$, $R_{b2}$ and $R_{b2'}$ are —(CH$_2$)—(CH(CH$_3$)$_2$);
$R_{c1}$ is —(CH$_2$CH$_2$O)$_q$CH$_2$CH$_2$— wherein q is 2;
$R_{c2}$ is selected from the group consisting of

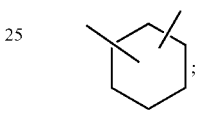

$s_1$=0.5; and $t_1$ is between 0.10 and 0.15, inclusive.
In an aspect of this invention, i=1, j=2, and k=0;
$R_{a1}$ is —(CH$_2$)$_8$—;
$R_{b1}$, $R_{b1'}$, $R_{b2}$ and $R_{b2'}$ are —(CH$_2$)—(CH(CH$_3$)$_2$);
$R_{c1}$ is —(CH$_2$CH$_2$O)$_q$CH$_2$CH$_2$— wherein q is 2;
$R_{c2}$ is

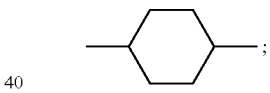

$s_1$=0.5; and $t_1$ is between 0.10 and 0.15, inclusive.
In an aspect of this invention, i=1, j=2, and k=0;
$R_{a1}$ is —(CH$_2$)$_8$—;
$R_{b1}$, $R_{b1'}$, $R_{b2}$ and $R_{b2'}$ are —(CH$_2$)—(CH(CH$_3$)$_2$);
$R_{c1}$ is —(CH$_2$CH$_2$O)$_q$CH$_2$CH$_2$— wherein q is 2;
$R_{c2}$ is selected from the group consisting of

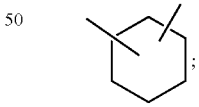

$s_1$=0.5; and $t_1$ is between 0.05 and 0.25, inclusive.
In an aspect of this invention at least one $R_{dk}$ is a straight chain polymer.
In an aspect of this invention at least one $R_{dk}$ is poly(ethylene glycol).
In an aspect of this invention at least one $R_{dk}$ is phosphoryl choline.
In an aspect of this invention, the polymer is about 0.05 mol % to about 5 mol % cross-linked.
An aspect of this invention encompasses an implantable medical device including a device body; and at least one coating layer including a polymer of any of the above mentioned aspects.

In an aspect of this invention, the at least one coating layer further includes a drug.

In an aspect of this invention, the implantable medical device is a stent.

An aspect of this invention encompasses a composition for controlled release of a drug including a plurality of particles, wherein the particles comprise a polymer of any of the above mentioned aspects of the present invention, and a drug.

In an aspect of this invention, the drug is selected from the group consisting of sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N-1-tetrazole)-rapamycin, and combinations thereof.

In an aspect of this invention the average particle size is about 1 nm to about 1000 µm.

In an aspect of this invention the average particle size is about 100 nm to about 100 µm.

In an aspect of this invention the average particle size is about 1 µm to about 30 µm.

In an aspect of this invention particle polydispersity is ±10% of average particle size.

In an aspect of this invention particle polydispersity is ±5% of the average particle size.

In an aspect of this invention the drug is substantially released within about 48 hours to about 12 months.

In an aspect of this invention the weight percent of drug in the particles or the at least one coating is about 1% to about 98%.

In an aspect of this invention the weight percent of drug in the particles or the at least one coating is about 1% to about 50%.

In an aspect of this invention, cumulative release after 24 hours is not more than 10% of total drug content.

In an aspect of this invention, cumulative release after 24 hours is not more than 20% of total drug content.

In an aspect of this invention the plurality of particles have a narrow polydispersity.

DETAILED DESCRIPTION

DISCUSSION

Figure 1:
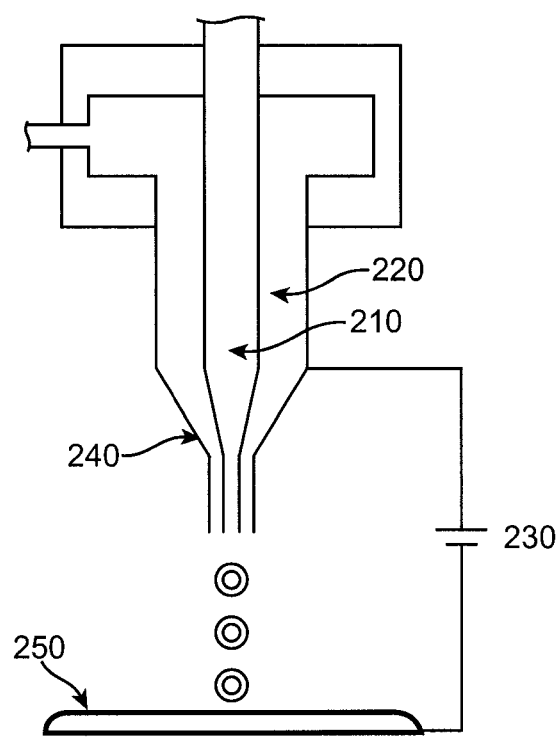
FIG. 1 is a depiction of a co-axial spray nozzle with an electrostatic field applied.

Use of the singular herein includes the plural and visa versa unless expressly stated to be otherwise. That is, "a" and "the" refer to one or more of whatever the word modifies. For example, "a drug" may refer to one drug, two drugs, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless it is expressly stated or obvious from the context that such is not intended.

As used herein, unless specified otherwise, any words of approximation such as without limitation, "about," "essentially," "substantially" and the like mean that the element so modified need not be exactly what is described but can vary from the description by as much as ±15% without exceeding the scope of this invention.

As used herein, "optional" means that the element modified by the term may or may not be present.

As used herein, "biocompatible" refers to a polymer that both in its intact, that is as synthesized state, and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, a material that is described as a layer or a film (e.g., a coating) "disposed over" an indicated substrate refers to, e.g., a coating of the material deposited directly or indirectly over at least a portion of the surface of the substrate. Direct depositing means that the coating is applied directly to the surface of the substrate. Indirect depositing means that the coating is applied to an intervening layer that has been deposited directly or indirectly over the substrate. A coating is supported by a surface of the substrate, whether the coating is deposited directly, or indirectly, onto the surface of the substrate. The terms "coating", "layer", and "coating layer" will be used interchangeably and refer to a layer, film, or coating as described in this paragraph. Unless the context clearly indicates otherwise, a reference to a coating, layer, or coating layer refers to a layer of material that covers all, or substantially all, of the surface, whether deposited directly or indirectly.

As used herein, "therapeutic agent," "drug" or "active agent," which will be used interchangeably, refers to any substance that, when administered in a therapeutically effective amount to a patient suffering from a disease or condition, has a therapeutic beneficial effect on the health and well-being of the patient. A therapeutic beneficial effect on the health and well-being of an individual includes, but it not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to an individual, known or suspected of being particularly susceptible to a disease, in a prophylactically effective amount, has a prophylactic beneficial effect on the health and well-being of the individual. A prophylactic beneficial effect on the health and well-being of an individual includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent," "drug" or "active agent" also refers to pharmaceutically acceptable, pharmacologically active derivatives of those drugs specifically mentioned herein, including, but not limited to, salts, esters, amides, prodrugs, active metabolites, analogs, and the like and to agents useful as diagnostic agents and vitamins.

As used herein, a polymer is a molecule made up of the repetition of a simpler unit, herein referred to as a constitutional unit. The constitutional units themselves can be the product of the reactions of other compounds. A polymer may comprise one or more types of constitutional units. As used herein, the term polymer refers to a molecule comprising from about 2 to about 1,000,000 units. An "oligomer" on the other hand refers to a molecule comprising less than 20 constitutional units, and as used herein is a sub-set of polymers. Polymers may be straight or branched chain, star-like or dendritic, or one polymer may be attached (grafted) onto another. Polymers may be cross-linked to form a network.

As used herein, "copolymer" refers to a polymer which includes more than one type of constitutional unit.

A poly(ester-amide) polymer refers to a polymer that has in its backbone structure both ester and amide bonds. A polyamide refers to a polymer that has in its backbone structure amide bonds. The polymers of this invention have the generic formula:

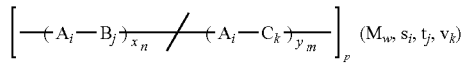

wherein the constitutional units are represented by $A_i$-$B_j$ and $A_i$-$C_k$ where the $A_i$ and $B_j$ react to form the constitutional unit represented by $A_i$-$B_j$ and $A_i$ and $C_k$ react to form the constitutional unit represented by $A_i$-$C_k$. The $A_i$ groups are derived from diacids, and the $B_j$ groups are derived from diamino esters. The group $C_k$ is a lysine group. Thus, each $A_i$ has the chemical structure:

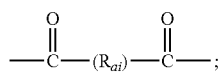

each $B_j$ has the chemical structure

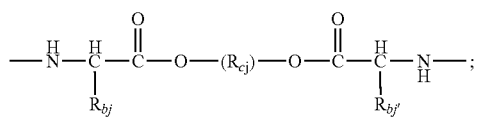

and
each $C_k$ has the chemical structure:

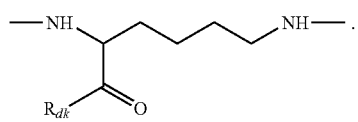

As noted above, the constitutional units themselves may be the product of the reactions of other compounds. For example, without limitation, a $B_j$ group above can comprise the reaction of an amino acid,

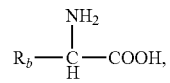

with a diol, HO—($R_c$)—OH, to give a diamino ester,

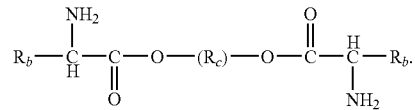

The diamino ester may be further reacted with a diacid,

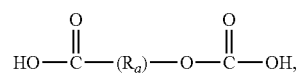

to give the constitutional unit, represented by $A_i$-$B_j$. The amine group, the carboxylic acid group or the hydroxyl group may be "activated," i.e., rendered more chemically reactive, to facilitate the reactions if desired; such activating techniques are well-known in the art and the use of any such techniques is within the scope of this invention.

While any amino acid may be used to construct a poly (ester-amide) of this invention, particularly useful amino acids are the so-called essential amino acids of which there currently 20: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. More recently selenoadenine has been found to be incorporated into a number of proteins and is included as a particularly useful amino acid of this invention. In naturally-occurring biological proteins, these amino acids appear as the l-enantiomeric isomers but for the purposes of this invention they may be used as their l- or d-enantiomers or as racemic mixtures.

On the lysine unit, represented by $C_k$, the $R_{dk}$ can be a drug, a peptide (which may a drug or a targeting moiety), a polymer, an oligomer or a brush polymer or oligomer, or another type of functional group. The polymer or oligomer may be hydrophilic or hydrophobic. $R_{dk}$ may also be an imaging agent such as a paramagnetic moiety that is capable of being imaged by MRI, or a contrast agent that is capable of being imaged by X-rays. $R_{dk}$ may also be a protective group to prevent the pendent acid functionality from participating in the polymerization reaction.

The linkage used to directly attach $R_{dk}$ to the carbonyl of the lysine may be an ester, a thioester, an amide, an anhydride, or an imide or $R_{dk}$ may be connected to the carbonyl through a spacer such as, without limitation, a C1-C12 alkyl or a poly(alkylene oxide) such as poly(ethylene glycol) or poly (propylene oxide).

As noted above, each $A_i$ and $B_j$ represents one or more different groups derived from diacids or derived from diamino esters, respectively, which may react to form the constitutional units, where i represents the $i^{th}$ type of $A_i$ group, j represents the $j^{th}$ type of $B_j$ group, and k represents the $k^{th}$ type of $C_k$ groups. Each polymer may have from 1 to 10 $A_i$ groups. Similarly, each polymer may have from 0 to 10 $B_j$ groups, and from 0 to 15 $C_k$ groups. A particular polymer may have fewer than the maximum, or 10, different $A_i$ groups. Thus if i=3, there is an $A_1$, $A_2$ and $A_3$ group. Similarly a particular polymer may have fewer different $B_j$ groups than the maximum, 10, and a particular polymer may have less than the maximum number of types of $C_k$ groups possible, that is 15. Similarly if j=2, there is a $B_1$ and a $B_2$ group, and if k=0 there are no $C_k$ groups. There must be at least one $A_i$ group, or i is at least one (1). In addition, there must be at least one $B_j$ group, or at least one $C_k$ group, or in other words, both j and k cannot equal zero (0).

The subscripts $x_n$ and $y_m$ are integers which represent the number of different possible types of $A_i$-$B_j$ and $A_i$-$C_k$ constitutional units in a polymer chain, respectively, and p is an integer which represents the average total number of constitutional units in an average polymer chain. Thus, each $x_n$ is an integer from about 0 to about 100, and $y_m$ is an integer from about 0 to 150, subject to the constraint that at least one $x_n$ or at least one $y_m$ is non-zero. The number of different $x_n$ groups is a function of the number of different $A_i$ groups and different $B_j$ groups as there is an $x_n$ for each $A_i$-$B_j$ group. For example if there are two $A_i$ groups and three $B_j$ groups, there will be six possible $A_i$-$B_j$ groups ($A_1$-$B_1$, $A_1$-$B_2$, $A_1$-$B_3$, $A_2$-$B_1$, $A_2$-$B_2$, $A_2$-$B_3$), and six $x_n$'s ($x_1$, $x_2$, $x_3$, $x_4$, $x_5$, $x_6$). The number of different $y_m$ groups is a function of the number of different $A_i$ groups and different $C_k$ groups as there is an $y_m$ for each $A_i$-$C_k$ group. For example, if there are two $A_i$ groups and three $C_k$ groups, there will be six possible $A_i$-$C_k$ groups ($A_1$-$C_1$, $A_1$-$C_2$, $A_1$-$C_3$, $A_2$-$C_1$, $A_2$-$C_2$, $A_2$-$C_3$), and six $y_m$'s ($y_1$, $y_2$, $y_3$, $y_4$, $y_5$, $y_6$). The average number of constitutional units in a chain, p, is an integer from 2 to about 4500.

Also in the above formula, each of the $s_i$, $t_j$, and $v_k$ represent the average mole fraction of each of the $A_i$, $B_j$, and $C_k$, respectively, which react to form the constitutional units. Each of the $s_i$, $t_j$, and $v_k$ is a number between 0 and 0.5, inclusive and subject to the constraints that $\Sigma_i s_i + \Sigma_i t_j + \Sigma_k v_k = 1.0$, and $\Sigma_i s_i = \Sigma_j t_j + \Sigma_k v_k = 0.5$ where each summation of $s_i$ is from 1 to the number of different $A_i$ groups (maximum of 10), each summation of $t_j$ is from 0 to the number of different $B_j$ groups (maximum of 10), and each summation of $v_k$ is from 0 to the number of different types of $C_k$ groups (maximum of 15). The values are also subject to the limitations that $\Sigma_i s_i > 0$, and either $\Sigma_j t_j > 0$ or $\Sigma_k v_k > 0$, or there is at least one non-zero $s_i$ along with at least one $t_j$ or at least one $v_k$ which is non-zero. Thus, in some embodiments, all $v_k$ may be 0, or $\Sigma_k v_k = 0$, or all $t_j$ may be 0 or $\Sigma_j t_j = 0$, but there are no embodiments where both $\Sigma_k v_k = 0$, and $\Sigma_j t_j = 0$. The mole fraction and the number of constitutional units are obviously related and it is understood that the designation of one will affect the other.

Other than the preceding provisos, $s_i$, $t_j$, and $v_k$ may be any mole fractions that provide a polymer that exhibits desirable properties for the particular use it is to put as set forth here, e.g., as part of a coating for an implantable medical device, as part of a drug delivery particle or for encapsulation of drug, subject to the limitations outlined above. However preferred values of $v_k$ are about 0.1 or less if the $C_k$ group is reacted as a free acid ($R_{dk}$="H" or hydrogen). Furthermore, it is preferred that the value of $v_k$ may be low for use with a more hydrophobic drug. Those of ordinary skill in the art will be able to manipulate the mole fractions, prepare the polymers and examine their properties to make the necessary determination based on the disclosures herein without resorting to undue experimentation.

In an aspect of the present invention, the polymers may be subject to the proviso that at least one $R_{ai}$ or at least one $R_{cj}$ is selected from the group consisting of

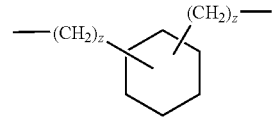

where z is 0, 1, or 2. The $R_{ai}$ is part of the $A_i$ group, and the $R_{cj}$ is part of the $B_j$ group. Thus, in those embodiments in which j=0 (or $\Sigma_j t_j = 0$), at least one $R_{ai}$ must be selected from the group outlined above.

The polymers of this invention may be regular alternating polymers, random alternating polymers, regular block polymers, random block polymers or purely random polymers unless expressly noted otherwise. A regular alternating polymer has the general structure: . . . x-y-z-x-y-z-x-y-z- . . . . A random alternating polymer has the general structure: . . . x-y-x-z-x-y-z-y-z-x-y- . . . , it being understood that the exact juxtaposition of the various constitution units may vary. A regular block polymer has the general structure: . . . x-x-x-y-y-y-z-z-z-x-x-x . . . , while a random block polymer has the general structure: . . . x-x-x-z-z-x-x-y-y-y-y-z-z-z-x-x-z-z-z- . . . . Similarly to the situation above regarding regular and alternating polymers, the juxtaposition of blocks, the number of constitutional units in each block and the number of blocks in block polymers of this invention are not in any manner limited by the preceding illustrative generic structures.

As noted above, the polymer represented by the above formula may be a random, alternating, random block or alternating block polymer. The term "–/–" means that the $A_i$-$B_j$ group may be attached to or reacted with another $A_i$-$B_j$ group, either including the same $A_i$ and $B_j$ or at least one of the $A_i$ and $B_j$ differ, or alternatively, a $A_i$-$C_k$ group. Thus the generic formula encompasses the following exemplary embodiments without limitation. In an exemplary but non-limiting embodiment, if the number of $A_i$ groups is 2 and the number of $B_j$ groups is 2, and the number of $C_k$ groups is 1, the following types of polymers are encompassed by the generic formula:

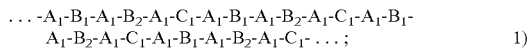

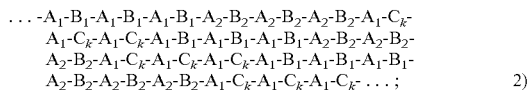

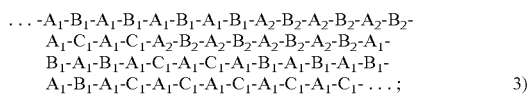

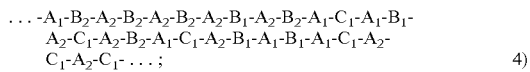

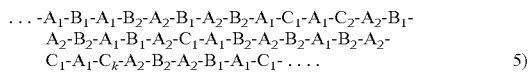

Thus, there are six potential constitutional units, $A_1$-$B_1$, $A_1$-$B_2$, $A_2$-$B_1$, $A_2$-$B_2$, $A_1$-$C_1$, and $A_2$-$C_2$. As the exemplary embodiments above illustrate, the polymer may be a completely random polymer, a regular alternating polymer, a random alternating polymer, a regular block polymer, or a random block polymer. As illustrated in polymer (2) above, only three groups are included $A_1$-$B_1$, $A_2$-$B_2$, and $A_1$-$C_1$. Such a polymer may be manufactured by reacting the separate blocks and then combining the blocks. Other polymers encompassed by the generic formula contain all six possible constitutional units, such as polymers (4) and (5).

Thus, the generic formula encompasses a polymer with only one type of constitutional unit. If there is only one $A_i$ and only one $B_j$ and no $C_k$ groups, there is only the $A_1$-$B_1$ unit. If there is only one $A_i$ and no $B_j$ groups and only one $C_k$ group, then there is only the $A_1$-$C_1$ unit. If there is only one $A_i$, only one $B_j$ and only one $C_k$ group, or only one $A_i$, only two $B_j$ groups, and not any $C_k$ groups, or two $A_i$ groups, and either only one $B_j$ group and not any $C_k$ groups, or only one $C_k$ group, and not any $B_j$ groups, there will be two potential constitutional units—$A_1$-$B_1$ and $A_1$-$C_1$ units, $A_1$-$B_1$ and $A_1$-$B_2$ units, $A_1$-$B_1$ and $A_2$-$B_1$ units, or $A_1$-$C_1$ and $A_2$-$C_1$ units, respectively. In general, the total number of potential constitutional units will be equal to the sum of the number of different types of $A_i$ groups times the number of different types of $B_j$ groups, plus the number of different types of $A_i$ groups times the number of different types of $C_k$ groups. As outlined above, not all potential constitutional units may be included in each embodiment.

In the above formula, $M_w$ represents the weight average molecular weight of the polymer of this invention. Again, while any molecular weight that results in a polymer that has the requisite properties to be used in the production of particles or use as a coating, at present the weight average molecular weight of a polymer of this invention is from about 10,000 Da (Daltons) to about 1,000,000 Da.

With regard to the synthesis of the polymers of this invention, it will be noted that no specific reactions or reaction conditions are exemplified herein. This is because the reactions and reaction conditions both for the preparation of constitutional units and for the preparation of the final polymer are standard organic and organic polymer chemistry well-known to those of ordinary skill in the art and, therefore, those skilled artisan would be able to prepare any of the compounds herein without undue experimentation based on the disclosures herein. However, when utilizing the $C_k$ at a level greater than about 10%, the $C_k$ group should not be reacted as a free acid but should include an $R_{dk}$ protective group. In other words, if $C_k$ is the free acid, then $v_k \leq 0.1$. In some embodiments, the $R_{dk}$ group will be altered after the polymerization reaction.

As used herein, the term brush polymer will refer to a polymer with a large number of branches. An example is shown below where "A" represents a constitutional unit:

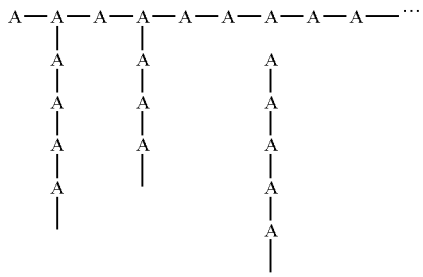

Although the example shown above utilizes only one type of constitutional unit, a brush polymer is not limited to one type of constitutional unit. The side chains, shown above as vertical chains, may be the same or a different composition than the backbone, shown above as a horizontal chain of constitutional units represented by "A." The side chains and the backbone may be of a different composition, and each may independently be composed of more than one constitutional unit. In some cases the side chains may differ in composition from each other.

As used herein, a "paramagnetic moiety" is one which is capable of being imaged by MRI. Non-limiting examples of paramagnetic materials can be found in U.S. Pat. No. 5,208,324, which is incorporated by reference as if fully set forth herein, including any drawings.

As used herein, a "contrast agent" is a substance which is capable of being imaged by an X-ray imaging device such as, but not limited to, a fluoroscope. The terms "contrast agent" and "radiopaque agent" are used interchangeably, and refer to the ability of a substance to absorb X-rays.

As used herein, a peptide sequence will refer to a molecule comprising from two to 50 amino acids. Chains of 50 amino acids or more are referred to herein as "proteins."

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. As used herein, "alkyl" includes "alkylene" groups, which refer to straight or branched fully saturated hydrocarbon groups having two rather than one open valences for bonding to other groups. Examples of alkylene groups include, but are not limited to methylene, —$CH_2$—, ethylene, —$CH_2CH_2$—, propylene, —$CH_2CH_2CH_2$—, n-butylene, —$CH_2CH_2CH_2CH_2$—, sec-butylene, —$CH_2CH_2CH(CH_3)$— and the like.

As used herein, "mC to nC," wherein m and n are integers refers to the number of possible carbon atoms in the indicated group. That is, the group can contain from "m" to "n", inclusive, carbon atoms. An alkyl group of this invention may comprise from 1 to 20 carbon atoms that is m may be 1 and n may be 20. Of course, a particular alkyl group may be more limited, for instance without limitation, to 3 to 8 carbon atoms, in which case it would be designate as a (3C-8C)alkyl group. The numbers are inclusive and incorporate all straight or branched chain structures having the indicated number of carbon atoms. For example without limitation, a "$C_1$ to $C_4$ alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$— and $(CH_3)_3CH$—.

As use herein, a cycloalkyl group refers to an alkyl group in which the end carbon atoms of the alkyl chain are covalently bonded to one another. The numbers "m" to "n" then refer to the number of carbon atoms in the ring so formed. Thus for instance, a (3C-8C)cycloalkyl group refers to a three, four, five, six, seven or eight member ring, that is, cyclopropane, cyclobutane, cyclopentane, cyclohexane, cycloheptane and cyclooctane.

As used herein,

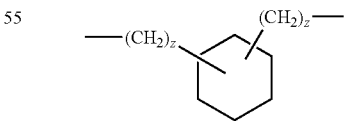

represents a cyclohexane group, optionally with a —$CH_2$— or a —$CH_2$—$CH_2$— group attached at any two locations on the ring, which is the optional groups may be attached at the 1 & 2, 1 & 3, or 1 & 4 positions. Alternatively, if z=0, the ring may attach to the other atoms in the molecule at the 1 & 2, 1 & 3, or 1 & 4 positions. Thus the following structures are encompassed:

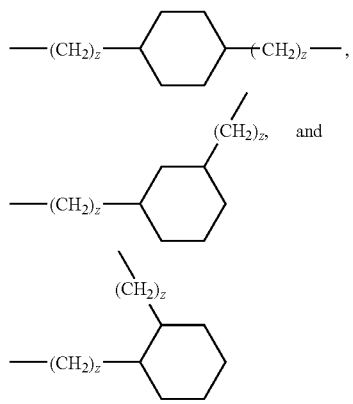

where z is 0, 1, or 2.

As used herein, "alkenyl" refers to an alkyl group that contains one or more double bonds.

As used herein, "alkynyl" refers to an alkyl group that contains one or more triple bonds.

Whenever a group of this invention is described as being "optionally substituted" that group may be unsubstituted or substituted with one or more of the indicated substituents.

Standard shorthand designations well-known to those skilled in the art are used throughout this application. Thus the intended structure will easily be recognizable to those skilled in the art based on the required valency of any particular atom with the understanding that all necessary hydrogen atoms are provided. For example, —COR, because carbon is tetravalent, must refer to the structure

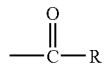

as that is the only way the carbon can be tetravalent without the addition of unshown hydrogen or other atoms.

Likewise, —O(CH)$_2$OP(=O)(O—)OCH$_2$CH$_2$N$^+$(CH$_3$)$_3$ refers to the structure $$-\!\!-\!O-\!\!\overset{H_2}{C}-\!O-\!\!\overset{\overset{O}{\|}}{\underset{O^-}{P}}-\!OCH_2CH_2\overset{\overset{CH_3}{|}}{\underset{CH_3}{N^+}}-\!CH_3.$$

Other such designations will be readily interpretable by those skilled in the art based on the discussion herein.

The designation of two or more alkyl moieties as alkyl$_1$, alkyl$_2$, etc., refers to alkyl groups may be the same or different.

As used herein, a "crosslink" refers to a joining of two separate chains of a polymer by reaction of non-terminal functional groups on the polymer with a multifunctional entity referred to as the cross-linking agent. As used herein, a "multifunctional crosslinking agent" is a compound having two or more functional groups that are capable of reacting with a functional group appended to the polymer backbone. As a non-limiting example, the functional group appended to the polymer backbone can be a hydroxyl, —OH, group and the multifunctional crosslinking agent can be a diisocyanate. The cross-linking reaction is shown schematically in Scheme 1:

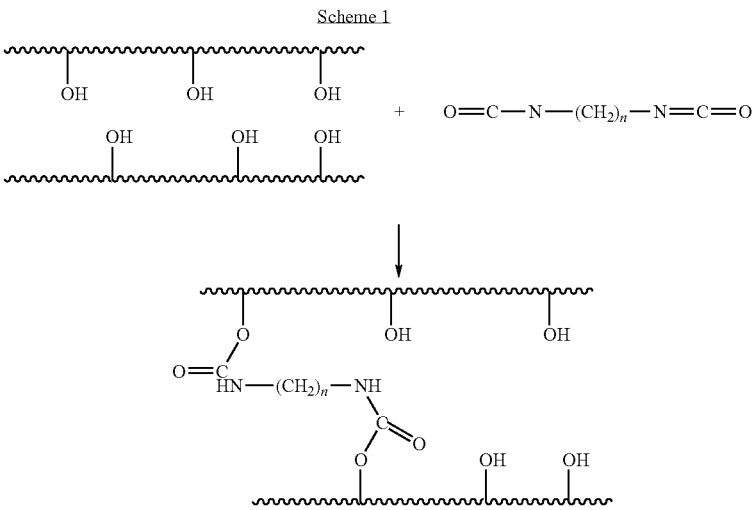

where the wavy line represents the polymer backbone and the crosslink comprises carbamate, —OC(O)NH—, groups. Of course, depending on how much diisocyanate is used, more than one hydroxyl group per polymer chain may become involved in crosslink formation.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, cerebrospinal fluid shunts, and intrauterine devices. An implantable medical device specifically designed and intended solely for the localized delivery of a drug is within the scope of this invention.

As used herein with respect to an implantable medical device, "device body" refers to an implantable medical device in a fully formed utilitarian state with an outer surface to which no coating or layer of material different from that of which the device is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of. Implantable medical devices can be made of virtually any material including metals and/or polymers. The material from which the device is manufactured is not a limitation on the use of the coatings of the present invention.

One type of implantable medical device is a stent. A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents and other medical devices may also be employed for the localized delivery of drugs to specific treatment sites in a patient's body. In fact, drug delivery may be the sole purpose of the stent or the stent may be primarily intended for another use such as those discussed above with drug delivery providing an ancillary benefit. A stent or other medical device intended solely or primarily for drug delivery is within the scope of the present invention.

A stent used for patency maintenance is usually delivered to the target site in a compressed state, often via a catheter, and then expanded to fit the vessel into which it has been inserted. Once at a target location, a stent may be self-expandable or balloon expandable.

As used herein, a material that is described as a layer or a film (e.g., a coating) "disposed over" an indicated substrate refers to, e.g., a coating of the material deposited directly or indirectly over at least a portion of the surface of the substrate. Direct depositing means that the coating is applied directly to the surface of the substrate. Indirect depositing means that the coating is applied to an intervening layer that has been deposited directly or indirectly over the substrate. A coating is supported by a surface of the substrate, whether the coating is deposited directly, or indirectly, onto the surface of the substrate. The terms "coating", "layer", and "coating layer" will be used interchangeably and refer to a layer, film, or coating as described in this paragraph. Unless the context clearly indicates otherwise, a reference to a coating, layer, or coating layer refers to a layer of material that covers all, or substantially all, of the surface, whether deposited directly or indirectly.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an adhesive intermediary layer between a device body and materials to be carried by the device body and is, therefore, applied directly to the device body. Examples, without limitation, of primers include silanes, titanates, zirconates, silicates, parylene, polyacrylates and polymethacrylates, with poly(n-butyl methacrylate) being a presently preferred primer.

As used herein, "drug reservoir layer" refers either to a layer of one or more drugs applied neat or to a layer of polymer or blend of polymers that has dispersed within its three-dimensional structure one or more drugs. A polymeric drug reservoir layer is designed such that, by one mechanism or another, e.g., without limitation, by elution or as the result of biodegradation of the polymer, the drug is released from the layer into the surrounding environment.

As used herein, "rate-controlling layer" refers to a polymeric layer that is applied over a drug reservoir layer to modify the rate of release into the environment of the drugs from the drug reservoir layer. A rate-controlling layer may be used simply to "tune" the rate of release of a drug to exactly that desired by the practitioner or it may be a necessary adjunct to the construct because the polymer or blend of polymers with which the drug is compatible with regard to coating as a drug reservoir layer may be too permeable to the drug resulting in too rapid release and delivery of the drug into a patient's body. In such case, a layer may be placed between the drug reservoir layer and the external environment wherein the layer comprises a polymer that, due to its inherent properties, and/or because it has been cross-linked, presents a more difficult barrier to traverse to an eluting drug. The rate-controlling propensity of this layer will depend, without limitation, on such factors as the amount of this polymer in the layer, the thickness of the layer and the degree of cross-linking of the polymer.

As used herein, a "topcoat layer" refers to an outermost layer, that is, a layer that is in contact with the external environment and that is coated over all other layers. The topcoat layer may be applied to provide better hydrophilicity to the device, to better lubricate the device or merely as a device protectant. The topcoat layer, however, may also contain drugs, in particular if the treatment protocol being employed calls for essentially immediate release of one or more drugs (these being included in the topcoat layer) followed by the controlled release of another drug or drugs over a longer period of time.

As used herein, "particle" may be a piece of matter held together by physical bonding of molecules, an agglomeration of particles held together by colloidal forces, and/or surface forces, or a piece of matter which is held together by chemical bonds, such as a cross-linked polymer network or one formed by ionic interactions, or a piece of matter held together by any combination of agglomeration, surface forces, colloidal forces, ionic interactions, and chemical bonds. For the purposes of this disclosure, a particle will be defined as ranging in size from less than a one tenth of a nanometer to several centimeters in size. In addition, a particle may include one or more types of constituent molecules. Particle in this context does not refer to sub-atomic particles such as electrons, protons, neutrinos etc.

As used herein, a "nano-particle" refers to a particle with a maximum cross-sectional, i.e., through-particle rather than along the surface, dimension of from 1 nm to 1000 nm.

As used herein, a "micro-particle" refers to a particle with a maximum cross-sectional dimension of from 1 um to about 1000 um.

The polydispersity of a group of particles represents the distribution of diameters within a particle group. Thus, the polydispersity can be represented by an average diameter and the standard deviation from the diameter. The average diameter can be a number average diameter, where the number average diameter=$\Sigma_i d_i n_i / \Sigma_i n_i$ where $n_i$ represents the number of particles with a diameter represented by $d_i$. Usually approximations are made and the distribution of particles by diameters is represented as a histogram, or in other words the particles are divided into smaller groups encompassing a smaller range of diameters and which is assigned a diameter near the center of that range. The surface area average diameter is determined by $(\Sigma_i f_i d_i^2)^{1/2}$, and the volume or mass average diameter is determined by $(\Sigma_i f_i d_i^3)^{1/3}$, where $f_i$ is $n_i/\Sigma_i n_i$. Thus, in the case of the surface area average, the weighting factor is the surface area represented by the class of particles of diameter $d_i$ while for the volume average diameter, the weighting factor is the volume represented by each class of particles of diameter $d_i$. Thus, since the surface area increases with diameter squared and the volume increases with diameter cubed, the surface area average diameter is greater than the number average diameter. The surface area diameter is in turn exceeded by the volume average diameter. The mass or weight average diameter is the same as the volume average diameter if the density of all of the particles is the same.

The standard deviation, which is a well-known statistical measurement, may be suitable for a narrow particle size distribution. Other measures of polydispersity include the d10 and d90 which refer to the diameters representing the threshold where 10% of the distribution falls below, and 90% of the distribution falls below, respectively. The average may be referred to as a d50. Thus for a number average, half or 50% of the number of particles have a diameter less than the d50. For an area average diameter, the d50 represents the point where half the surface area represented by the group of particles is below the d50.

Another means for determining the average diameter is by the use of dynamic light scattering, which is also called photon correlation spectroscopy, and measures the diffusion of the particles in solution. The average diameter is the mean hydrodynamic diameter, and is close to the volume-average diameter. One method is outlined in the International Standards Organization ("ISO") 13321.

As used herein, a "narrow polydispersity" will refer to one in which the at least 80%, preferably 90% and most preferably at present at least 95% are within ±10%, preferably at present within 5% of the average particle size. The 80%, 90%, or 95% refers to the number of particles if a number average diameter or the weight of the particles if a weight average diameter is used, or the intensity if an intensity average diameter such as that obtained from dynamic light scattering is used. If photo correlation spectroscopy is used, then the percent refers to the cumulative intensity from the dynamic light scattering.

As used herein, "degradation time" refers to the time for a biodegradable particle implanted in a vessel to substantially completely biodegrades in vivo.

As used herein, "release rate" refers to the speed of drug release from a particle or a coating per unit of time, for example without limitation 0.1 mg per hour (0.1 mg/hr) or 100 mg per day. With respect to a coating, the release rate may be expressed as the mass per unit time per unit surface area such as, without limitation, 0.1 mg/(hr-mm$^2$). A "cumulative release" rate or profile may also be expressed as % drug released over time, ie 15% after 24 h or 30% after 3 days where the denominator is the total drug content. The total drug content, or total content, may be determined by an assay of a number of units, the theoretical drug content, the target or objective drug content, or the label claim.

As used herein, "release duration," refers to the total time over which a drug is released in a therapeutically effective amount from a particle Thus, for example without limitation, a drug release range of, say, 1 hour to 72 hours means that a therapeutically effective amount of the drug is released over that time period.

As used herein, "burst release" refers to the uncontrolled release of drug within a very short time, relative to the desired release duration time, after implantation of a drug-containing particle in a patient. In some embodiments, "burst release" refers to the initial rapid release of drug within the first 24 hrs, or the cumulative release after a 24 hour time period.

As used herein, "substantially released" refers to a cumulative release of the drug of about 80% or more.

With regard to the present invention, zotarolimus and everolimus, both immunosuppressive macrolide antibiotics, are presently preferred drugs for use with the drug delivery particles and coatings of the present invention.

Various aspects of the present invention include both cross-linked and uncross-linked polymers. These polymers may be used for the fabrication of drug delivery particles, or coatings.

The particles herein may be solid constructs with drug dispersed within the matrix or they may be core/shell constructs such as, without limitation, micelles, worm micelles, liposomes and polymersomes.

A micelle is a spherical colloidal core/shell nanoparticle spontaneously formed by many amphiphilic molecules in an aqueous medium when the Critical Micelle Concentration (CMC) is exceeded. The shell comprises a monolayer of the amphiphilic molecules. Amphiphilic molecules have two distinct components, differing in their affinity for a solute, most particularly water. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants."

Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Drugs suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the drug. Micelles are of nanoscale size, generally from about 5 nm to about 50 nm.

The problem with micelles formed from relatively low molecular weight surfactants is that their CMC is usually quite high so that the formed micelles dissociate rather rapidly upon dilution, i.e., the molecules head for open places at the surface of the water with the resulting precipitation of the drug.

Polymeric micelles have been prepared that exhibit CMCs as low as $10^{-6}$ M (molar). Thus, they tend to be very stable while at the same time showing the same beneficial characteristics as surfactant micelles. It is believed that if manufactured as a block copolymer, the poly(ester-amide) and poly(amide) polymers of the present invention may be used to form polymeric micelles.

In addition to the classical spherical micelles described above, drugs may be delivered using the methods of this invention in compositions comprising synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. A representative description of worm micelle formation, characterization and drug loading can be found in Kim, Y., et al., *Nanotechnology,* 2005, 16:S484-S491.

A liposome is a core/shell construct in which the shell comprises a bilayer rather than a monolayer. Liposomes may be unilamellar, composed of a single bilayer, or they may be multilamellar, composed of two or more concentric bilayers. A phospholipid bilayer is formed from two layers of phospholipid molecules. Phospholipids are molecules that have two primary regions, a hydrophilic head region comprised of a phosphate of an organic molecule and one or more hydrophobic fatty acid tails. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere.

A core/shell construct similar to that of a liposome but made of polymers other than phospholipids or sphigolipids is called a polymersome. Block copolymers of this invention may be used to form polymersomes.

For drug delivery particles and coatings for medical devices, the polymers of the present invention are particularly advantageous because the ability to optimize the physical and chemical properties of the polymer. The constitutional units, $A_i$-$B_j$ and $A_i$-$C_k$ may be altered through the choice of amino acids, the diol used to form ester linkages between amino acids (the $R_{cj}$ group) and the type of diacid group ($R_{ai}$ group) used to create amide linkages. Each of the preceding groups may be modified with substituent groups to further optimize the physical and chemical properties of the polymer with regard to, without limitation, drug miscibility and release properties and biodegradation rate of the polymer. In particular, $R_{dk}$ may be varied to provide the polymers with a broad range of characteristics.

The polymers of the present invention may be composed of only one constitutional unit, or may include multiple constitutional units (copolymers). For preparation of micelles or polymersomes, block copolymers are presently preferred while for solid particles random copolymers are presently preferred.

Choice of constitutional units will, of course, affect the biodegradation rate particles or coatings of this invention. For example, without limitation increasing hydrophilicity, and thus water absorption leads to quicker degradation of particles or a coating layer, and can be achieved, without limitation, by increasing the mole fraction of free acid-containing $C_k$ groups. The time to biodegrade is also impacted by the molecular weight.

Through the choice of the constitutional units, the glass transition temperature ($T_g$) of the poly(ester-amide) or poly(amide) polymer may be adjusted to be above or below the temperature of use, which would be about 37° C. for a human, depending on desired particle or coating characteristics. For example, if the polymer has a $T_g$ that is below 37° C., the polymer will be in its amorphous state when implanted which will in general favor diffusion of a drug out of the particles or a coating whereas a $T_g$ above 37° C. will result in the particles or the coating being glass-like, which will impede diffusion of drugs from the polymer matrix.

In addition, a higher glass transition temperature or a higher melting temperature ($T_m$) may lessen the impact that ethylene oxide sterilization has on the polymer in terms of uptake of ethylene oxide and/or water during the sterilization process. The absorption of ethylene oxide and/or water may lead to physical changes in the particle as a result of polymer swelling. It is believed that the choice of some constitutional units, particularly the L-phenylalanine as the amino acid of an $A_i$ group, may lead to partial crystallization of the poly(ester-amide) or poly(amide) polymer as the phenylalanine groups can form a lamellar structure. Crystalline regions may improve particle response to sterilization as there is less absorption of water and ethylene oxide into these regions. Thus, particles including a high glass transition temperature poly(ester-amide) or poly(amide) polymer may be successfully sterilized with limited impact of the properties of the particle.

Through the choice of the constitutional units, the drug miscibility and drug release characteristics may be optimized. Drug miscibility may be estimated using solubility parameters, such as Hansen's or Hildebrand's. The latter is determined using the equation:

$$\delta = (\Delta E/V)^{1/2}$$

where $\delta$ is the solubility parameter, $(cal/cm^3)^{1/2}$;
$\Delta E$ is the energy of vaporization in cal/mole; and
$V$ is the molar volume in $cm^3$/mole.

Alternatively, the $\delta$ value for polymers may be obtained from experimental measurements. For polymers, such experiments often include measurement of the degree of swelling or absorption of solvent of a known $\delta$ value. The estimated solubility parameter of the drug can be compared to the solubility parameter of the polymer. The solubility parameter for the polymer can be estimated based upon the constitutional units $A_i$-$B_j$ and $A_i$-$C_k$. By choosing the constitutional units $A_i$-$B_j$ and $A_i$-$C_k$, the hydrophilicity of the polymer may be varied. As outlined above, inclusion of the $A_i$-$C_k$ constitutional unit, and more of the $A_i$-$C_k$ constitutional unit, increases the hydrophilicity of the polymer if the $C_k$ is a free acid. Thus, aspects of the present invention allow for the production of particles to encapsulate drugs, or coatings for controlled release of drugs, which are quite hydrophobic, such as everolimus, and small hydrophilic drugs such as peptides, proteins, genes, and other water-soluble molecules. In addition, the variations in miscibility can be obtained for the polymers utilized in the present invention while maintaining desirable physical properties such as resistance to ethylene oxide sterilization.

In has surprisingly been found that use of an $R_{cj}$ group which is a cyclohexyl group

or a cyclohexyl with the methylene groups attached in the 1 and 4 positions

provide miscibility with and controlled release of everolimus, a hydrophobic drug, while maintaining desirable physical properties. Specifically, when —$CH_2CH(CH_3)_2$ is used for the $R_{bj}$ and $R_{bj'}$ groups of the $B_j$ groups, different ratios of cyclohexane

to hexane (—$(CH_2)_6$—) in the $R_{cj}$ groups and different lengths of alkyl chains for the $R_{ai}$ group of the $A_i$ group in the polymer can drastically impact the release of everolimus from a coating made from the polymer as well as the glass transition ($T_g$) temperature of the polymer. As shown in Example 1, the use of a 50:50 ratio of n-hexane (—$(CH_2)_6$—) to cyclohexane

for the $R_{cj}$ groups and —$(CH_2)_8$— for the $R_{ai}$ group or a 25:75 ratio of triethylene glycol (—$(CH_2CH_2O)_qCH_2CH_2$— wherein q is 2) with cyclohexane

and —$(CH_2)_8$— for the $R_{ai}$ group both result in a polymer which when used in a coating for the controlled release of everolimus exhibits a 20% cumulative release after 3 days. As shown in Example 1 below changing the ratio of $R_{cj}$ groups or the length of alkyl chain in the $R_{ai}$ group results in a polymer exhibiting much greater or much lower cumulative release of everolimus after 3 days if used as the polymer in a polymeric drug reservoir. Thus, it is believed that the use of

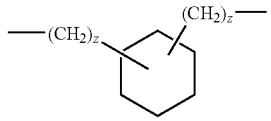

where z is 0, 1, or 2, as a $R_{ai}$ group in the polymers of the present invention would have similar results. In other words, the use of the cyclohexane group

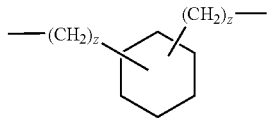

where z is 0, 1, or 2) as either a $R_{cj}$ group or a $R_{ai}$ group may allow for "tuning" the miscibility and release rate characteristics of a polymer to a particular drug while maintaining acceptable mechanical properties.

Drug release rates and durations of the present invention is impacted not only by the choice of the constitutional units $A_i$-$B_j$ and $A_i$-$C_k$ in the polymer, but also by other properties of the particles, and other properties of the coating layer. The ratio of drug to polymer and the inclusion or exclusion of additional materials both impact drug release. Some aspects of the present invention utilize particles or coatings including less than about 5% drug, about 5% to about 10% drug, about 10% to about 15% drug, about 15% to about 20% drug, about 20% to about 25% drug, about 25% to about 30% drug, about 30% to about 40% drug, about 40% to about 50% drug, about 50% to about 60% drug, about 60% to about 75% drug, about 75% to about 90% drug, and more than about 90% drug. The remainder of the material included in the particles and coatings may be all, or substantially all, polymer, or may include other materials such as fillers, binders, carriers, and/or plasticizers. Also other polymers such as those set forth below may be included in the particles and coatings of this invention. In preferred embodiments, the particles and coatings are made from biodegradable polymers.

For drug delivery particles, drug release is also impacted by particle size. In some aspects of the present invention, the particles will be in a size range classified as micro-particles while in other aspects the particles will be in a size range classified as nano-particles. The particle size may vary from less than 1 nm up to 1 mm depending upon the specific application. Other suitable size ranges include about 1 nm to about 10 nm, about 5 nm to about 20 nm, about 5 nm to about 50 nm, about 50 nm to about 100 nm, about 100 nm to about 1000 nm, about 0.1 μm to about 15 μm about 0.5 μm to about 5 μm, about 1 μm to 20 μm, about 10 μm to about 100 μm, about 50 μm to about 250 μm, about 100 μm to about 500 μm, and about 500 μm to about 1000 μm. In some aspects of the current invention, the particles will be of a size that is larger than microparticles.

In general a larger size will provide a longer duration of delivery. Small particles are more suitable for device compatibility. Thus, for some applications a particularly advantageous size is from about 1 μm to about 3 μm. Particles in the size range of about 1 μm to about 3 μm can easily be injected through a small diameter, very long needle or catheter without clogging. Another particularly advantageous particle size range of interest is from about 10 µm to about 15 µm, as these particles may be trapped in the microvasculature. However, a larger catheter (3-4 French) is required for delivery. The polydispersity of the particles is also a factor as a lower polydispersity provides a more reproducible release rate.

Particles which are polymersomes and micelles must be manufactured from polymers of the present invention which are diblock copolymers, or of a composition that is close to being a diblock copolymer, that is each of the "blocks" may contain another constitutional unit, but the properties of the each "block" are primarily hydrophobic or primarily hydrophilic. With respect to polymersome, the polymers of the present invention can be altered by the choice of constitutional groups and the length of the blocks such that polymerosomes can be substantially more robust that liposomes. In addition, the ability to control completely the chemical nature of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

With respect to the coatings of the present invention, the existence of other coating layers may impact the drug release from a coating layer. There may be multiple coating layers including a reservoir layer, a primer layer, a release-rate controlling layer, and a topcoat layer. The poly(amide) and poly (ester-amide) polymers of the present invention may be included in any of the above coating layers. In some embodiments, only one coating layer may be disposed over the implantable medical device. The one coating layer may be a drug reservoir layer. In some embodiments, there may be more than one coating layer including any combination of the above layers. In some embodiments, the drug reservoir layer may also control drug release, and therefore, there may be an optional primer and/or topcoat coating layer disposed over the device. In other embodiments, there may be a rate-controlling layer and a drug reservoir layer and optionally a primer and/or topcoat layer. In some embodiments there may be more than one drug reservoir layer. Similarly, in some embodiments there may be more than one release control layer. In some embodiments there are additional coating layers not specifically labeled or identified as above. For example two or more drug reservoir layers each including a drug may be separated by an intervening layer to limit interaction between the two drugs during manufacturing and storage. Any number of layers may be included above or below the drug reservoir layer.

With respect to coatings, the coating thickness has an impact on drug release as well as other coating properties. The various embodiments of the present invention include a coating including a poly(amide) and/or a poly(ester-amide) polymer of the present invention with a range of thickness over an implantable device. In certain embodiments, the coating that is deposited over at least a portion of the implantable device has a thickness of ≤about 30 micron, or ≤about 20 micron, or ≤about 10 micron, or ≤about 5 micron, or ≤about 3 micron. These dimensions apply to each of the individual layers if more than one layer is deposited on the surface of the medical device, either directly or indirectly.

The release of drug from the particles may occur by any number of mechanisms which depends, in part, on the type of particle. A drug may be distributed throughout a solid particle matrix. Distribution may be substantially homogeneous or non-uniform. The drug may be released by any number of mechanisms. In some embodiments, the drug may be released as the matrix polymer dissolves. In other embodiments, the drug may diffuse through the matrix into the surrounding tissue. In other embodiments, the drug may diffuse through the matrix and/or diffuse through pores formed when the drug is dissolved from the matrix closer to the surface.

The drug delivery particles may encapsulate one or more drugs by having an outer shell of polymer and optionally other materials, with an inner compartment containing one or more drugs. Such particles with an outer shell without drug are typically referred to as reservoir type or shell/core particles, or a "micro encapsulation." If the exterior coating does not contain a drug, it may serve as a rate-controlling membrane as the drug must diffuse through the membrane, and the drug may release essentially at a constant rate (aka "zero-order") over time until the drug in the interior, or reservoir, starts to become depleted. In some embodiments, drug may be included in the outer coating, typically at a lower concentration than the interior of the particle.

Similarly different mechanisms of release as well as release patterns may be seen in polymer coatings, wherein the drug is released by diffusion through the polymer of the coating or through pores formed as a result of drug release, or as the coating dissolves and/or biodegrades. However, with respect to coatings, the drug is generally distributed uniformly, or substantially uniformly.

Drug release from particles or coatings is also impacted by biodegradation. The rate of the biodegradation of the polymer, and thus the particle or coating which includes the polymer, is a function of a number of factors. One factor is the particular chemistry of the polymer utilized in the particle. In general, polymers which are more hydrophilic will absorb more water and lead to quicker degradation. As noted, the inclusion of more $C_k$ groups, particularly as the free acid, increases the water absorption and thus the rate of biodegradation. Biodegradation rate is also influenced by the molecular weight of the polymer with higher molecular weight polymers exhibiting longer biodegradation times. The size of the particle, or thickness of the coating, also impacts the biodegradation rate with larger particles or thicker coatings generally taking a longer time to biodegrade (assuming similar drug loadings and other properties).

In some aspects of the present invention, the particles may be coated with a layer which impacts drug release rate and biodegradation rate. The particle outer coating may be polymeric or non-polymeric.

As noted above, the particles of the various aspects of the present invention may have a narrow polydispersity. Narrow polydispersity provides for several advantages. First, as degradation is in part a function of particle size, the degradation of the particles is more reproducible if they are monodisperse that is all of substantially the same size. In some aspects the ratio of the d90 to the d10, by use of any of the standard particle size measurements, may be 5, may be 4, may be 3, or may be 2, or maybe 1.

The release profile of the drug from the particle or a coating may be, but is not limited to, zero-order release, exponential decay, step-function release or other release profiles that may be desired. The release profile is largely dependent upon the particle or coating construct and the type of polymers used to form the particle. The term "pulse release" generally refers to a release profile of a drug that features a sudden surge in the release rate followed by return of the release rate to a lower level followed by yet another sudden surge in cyclic repetition. The terms "zero-order release", "exponential decay" and "step-function release" as well as other sustained release profiles are well known in the art. As outlined above, as used herein, "burst release" refers to the uncontrolled release of drug within a very short time, relative to the desired release duration time, after implantation of a drug-containing particle in a patient. While burst release may at times be a desired release characteristic, in general it is undesirable in that, for instance, it might result in release of a toxic amount of a drug.

Thus, in aspects of the present invention, burst release for drug delivery particles may be no greater than about 90%, preferably no greater than about 50%, more preferably no greater than about 20%, and most preferably at present no greater than about 10%.

Thus, in aspects of the present invention, burst release for drug from a polymeric drug reservoir layer including a polymer of the present invention may be no greater than about 90%, preferably no greater than about 50%, more preferably no greater than about 20%, and most preferably at present no greater than about 10%.

Improved miscibility of the polymer and drug allows for better control of the burst release as the drug does not phase separate and is less inclined to partition to the surface of the particle or coating. The physical and chemical variability of the poly(ester-amide) and poly(amide) polymers of the present invention permits a broad range of drug miscibility, or compatibility, not available with other polymers.

In some aspects of the present invention, the duration of the drug release from either the particles and/or a coating layer, that is the time during which a therapeutically effective amount of the drug is released, may range from about 24 hours to about 1 week, from about 48 hours to about 1 week, from about 72 hours to about 2 weeks, from about 1 week to about 1 month, from about 2 weeks to about 3 months, from about 24 hours to about 12 months, from about 1 month to about 12 months, from about 1 month to about 24 months, from about 2 months to about 12 months, or from about 1 month to about 6 months.

In some aspects of the present invention, the time required for particles or coating layers (or the polymer included in the coating layer) of the present invention to substantially biodegrade, may range from about 24 hours to about 1 week, from about 48 hours to about 1 week, from about 72 hours to about 2 weeks, from about 1 week to about 1 month, from about 2 weeks to about 3 months, from about 24 hours to about 12 months, from about 1 month to about 12 months, from about 1 month to about 24 months, from about 2 months to about 12 months, or from about 1 month to about 6 months.

Another aspect of the various drug delivery particles of the present invention involves the choice of $R_{dk}$. As outlined above, $R_{dk}$ may constitute a variety of substituents. Among those is a peptide sequence that can bind to an inflammation site, a poly(ethylene glycol) group to enhance hydrophilicity or a phosphoryl choline to enhance biocompatibility and bioabsorbability.

Various methods are known for coating of medical devices such as stents. Each coating layer can be disposed over the implantable device (e.g., a stent) by dissolving or dispersing the polymer, optionally with one or more other polymers and/or other additives, and optionally including a drug, in a solvent, or a mixture of solvents (where the solvent is a fluid), and disposing the resulting coating solution over the stent by procedures such as spraying or immersing the stent in the solution. Such coating procedures are well-known in the art. Other procedures are also possible. After the solution has been disposed over the stent, the solvent is removed, or substantially removed, by evaporation. When the solvent is removed, what is left is the solid material which forms a layer, film, or coating on the surface of the implantable medical device, either directly or indirectly. The process of drying can be accelerated if the drying is conducted at an elevated temperature, and/or with the addition of a flow of air (or flow of another gas or a supercritical fluid) over or past the device to enhance mass transfer of the solvent.

The complete implantable medical device (such as a stent) coating may be optionally annealed or subjected to heat treatment for a limited time after the coating has been applied.

There are various methods that are well known in the art by which the solid matrix particles or core/shell particles of this invention can be manufactured. Such methods include emulsion solvent evaporation methods, phase separation methods, interfacial methods, extrusion methods, molding methods, injection molding methods, heat press methods, coating or layering processes, spray drying, electrospraying, membrane emulsion, precision particle fabrication and so forth. Specific examples of manufacturing processes for matrix type particles may be found in the following U.S. Pat. Nos. 4,954,298; 6,528,093; 4,897,268; 4,293,539; 6,224,794; 7,060,299; and 7,048,947, each of which is incorporated by reference as if fully set forth, including any drawings, herein. Specific examples for the manufacture of core/shell particles, may be found in the following U.S. Pat. Nos. 6,767,637 and 4,622,244 that likewise are incorporated by reference as if fully set forth, including any drawings, herein. None of the preceding exemplary art is intended, nor should it be construed, to limit the present invention.

One method that is particularly suitable for the preparation particles is emulsion solvent evaporation. The first step in such a method is dissolving the polymers in an organic solvent that is immiscible in water. Typical concentrations for solutions are about 5 w/w %, or up to about 10 w/w %, while typical concentrations for dispersions are up to about 5 w/w %. Solvents include, but are not limited to, methylene chloride, dichloromethane, chloroform, or ethyl acetate. The next step is to create an emulsion of the organic solvent phase in an aqueous phase. A typical organic solvent:aqueous solvent ratio is about 1:2 and may go up to 1:20. The creation of the emulsion requires energy input which may be, without limitation, supplied by an ultra sonicator or a homogenizer. Typically, the aqueous phase contains emulsifying agents. Exemplary emulsifying agents include, but are not limited to, polyvinyl alcohol, polyvinyl pyrrolidone (povidone as per the United States Pharamcopeaia), sodium lauryl sulfate, sodium cholate, TWEEN 80™ (sorbitan monooleate polyethenoxy ether), diacetyl tartaric acid ester of mono- and di-glycerides, glycerol monostearate, glycerol monooleate, glycerol behenate, lecitihin, monosodium phosphate derivatives of mono and di-glycerides, phosphatidylcholine, stearylamine, and eoxycholic acid.

The organic solvent is evaporated at a pressure ranging from atmospheric to reduced, i.e., under vacuum. During solvent evaporation, the emulsion is continuously stirred. The resulting particles are suspended in the aqueous solution. For the incorporation of hydrophobic drugs, the drug is dissolved in the organic phase which also includes the polymer. As a result of the processing outlined above, the drug is encapsulated in the particle with the particles suspended in the aqueous solution at the end of the process.

The emulsion solvent evaporation method is slightly different when the encapsulation of a hydrophilic drug in the particle is desired. Prior to the first step outlined above, that is the dissolution of the polymer in an organic solvent, the hydrophilic or water soluble drug is dissolved in an aqueous solution. The same emulsifying agents described above may be used. The ratio of aqueous to organic phase in the initial emulsion is from about 1:2 up to 1:20 or more. The aqueous solution including the dissolved drug and surfactants is then emulsified in the organic phase. Here, in contrast to the situation above, the organic phase is the continuous phase and the aqueous drug-containing phase is the discontinuous or discrete phase. Then the same steps are followed as outlined above resulting in the formation of a double emulsion. An aqueous phase is emulsified in an organic phase which in turn is emulsified in a second aqueous phase. In the second emulsion, a typical ratio of the "organic phase" (actually the first emulsion) to the aqueous phase is from about 1:100 up to 1:500 or higher. As outlined above, the evaporation occurs with continuous stirring.

For both emulsion solvent evaporation methods, more vigorous stirring during the solvent evaporation phase generally leads to smaller particle sizes. Also, the choice and quantity of surfactants and emulsifying agents impact the stability of the emulsion, the particle size of the resulting particles, and may impact drug release rate and/or duration.

For both emulsion solvent evaporation methods outlined above, if a peptide or protein is encapsulated in the particle, the solvent evaporation operation as well as other operations should occur at lower temperatures to avoid denaturing the protein or peptide.

In either method of emulsion solvent evaporation outlined above, the final step of removing the solvent may be accomplished utilizing supercritical fluid solvent extraction instead of evaporation. Advantages of supercritical fluid solvent extraction are vastly improved and tunable selectivity, lower processing temperatures, lower levels of residual solvents, and the possibility of continuous production.

Another method that is particularly suitable for the preparation of particles is precipitation. This method involves dissolving the polymer and drug in an organic phase which is miscible in water. The solution is added to an aqueous solution containing a colloid stabilizer, a non-solvent for the polymer and the drug, such that the polymer and drug precipitate to form particles. The organic solvent is removed from the particles by either evaporation or dialysis.

Another method particularly suitable for the preparation of particles is spray drying. Equipment to accomplish spray drying is well known in the art. An example, without limitation, of a spray drying apparatus at the laboratory scale is a Buchi MINI SPRAY. The polymer and the drug are dissolved in a solvent, preferably one with a high volatility. Additionally a surfactant may be added to the solution to prevent or limit particle aggregation. The solution is then sprayed into a heated chamber to quickly remove the solvent and precipitate particles. Pressurized air or another gas is also used to atomize the solution (or dispersion) that is sprayed into the chamber. The temperature of the chamber utilized depends upon the type of solvent used as well as the polymer, drug, and/or other materials used to form the particles. The temperature should be chosen to be high enough to evaporate the solvent but not so high that the drug is degraded and/or the temperature exceeds the glass transition temperature of the polymer. The particle size and other characteristics of the particles can be optimized by adjusting the nozzle orifice size and/or type of nozzle used, the flow rate of the solution, the air pressure for the atomization, and the temperature at the spray nozzle. Typical flow rates, without limitation, are about 0.2 to 5 ml/hour on a laboratory scale. The solution viscosity should be about 20 cP or lower. Typically the polymer molecular weight is about 50 kDa or less, but this will depend upon the chemistry of the polymer used, the solvent, and the concentration of polymer in the solvent.

A particularly useful variation of the spray drying technique involves laminar jet technology which can be combined with electrostatic field, vibrating nozzle, and coaxial fluid (gas or non-solvent) technology. A typical but not-limiting intensity of the electrostatic field is 2-15 kV.

A vibrating nozzle enhances the electrostatic dispersion of solutions and allows for the production of small, highly charged droplets which results in spherical particles. A typical but not-limiting range of nozzle vibration for a vibrating nozzle is 60 to 120 kHz. A vibrating nozzle allows a laminar jet of fluid to be broken into droplets.

Co-axial fluid technology involves two immiscible fluids. FIG. 1 is an illustration. Centerfluid 210 containing the drug and outerfluid 220 flows through in concentric annuli. As FIG. 1 illustrates, this can be combined with electrostatic charge where there is a voltage supplied by high voltage supply 230 across nozzle tip 240 to substrate 250. The advantage of this technology is that particles with a very narrow polydispersity can be obtained. As noted above, a narrow polydispersity is desirable as it leads to a more reproducible drug delivery rates and biodegradation rates.

Figure 2:
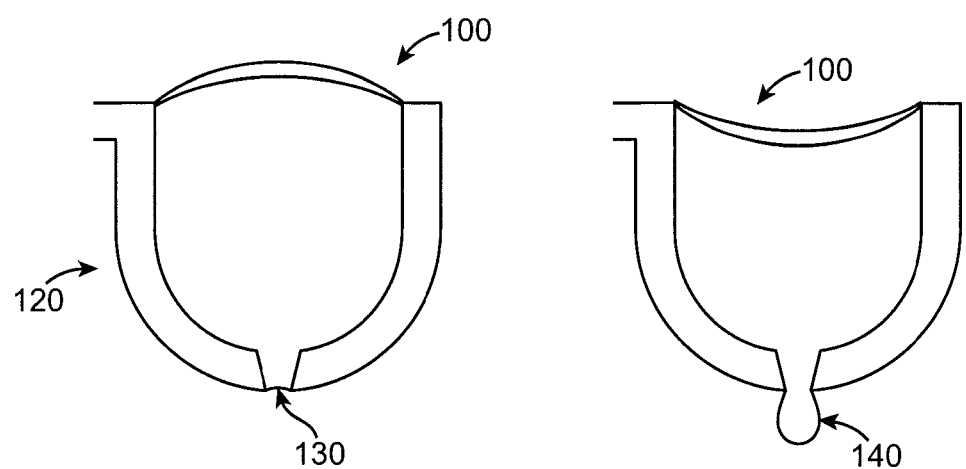
FIG. 2 is a depiction of a piezo nozzle.

Another technique for production of uniform particles is use of a piezo nozzle such as those used in the ink-jet printing industry. An example of a piezo nozzle is illustrated in FIG. 2. The use of a piezo nozzle involves the application of an electric charge to piezo crystal 100 that forms the top of fluid reservoir 120 which has orifice 130 in the bottom. Piezo crystal 100 flexes with the application of an electric charge and as a result forces droplet 140 out of the reservoir.

Particles with a narrow polydispersity can be obtained by the combination of the electrostatic field with the piezo nozzle, or alternatively the combination of the electrostatic field with the co-axial fluid technology.

Precision particle fabrication is a technology that combines the laminar jet technology and the vibrating nozzle (Berkland et al., "Precision Polymer Microparticles for Controlled Drug Delivery," *American Chemical Society Symposium* 897: *Carrier Based Drug Delivery*, Chapter 14, pages 197-213, American Chemical Society, 2004). Precision particle fabrication involves spraying a solution or dispersion of polymer and drug through a small nozzle to form a stable laminar jet. The jet is disrupted by acoustic energy provided by a piezoelectric transducer which is driven by a wave generator. The jet is disrupted by the acoustic energy and breaks into droplets. In addition, an annular stream of a second fluid moving at a high velocity can help to make particles smaller than the nozzle opening size (Berkland et al., "Fabrication of PLG Mircrospheres with Precisely Controlled and Monodisperse Size Distributions," *Journal of Controlled Release*, 73: 59-74 (2001)). The ratio of the volume average diameter to the number average diameter for particles manufactured with this method ranged from 1.002 to 1.015.

Other techniques for manufacturing particles with a narrow polydispersity include membrane emulsification, which involves use of a specially made porous glass membrane (Nakashima et al., *Advanced Drug Delivery Reviews*, 45 (2000), 47-56). The oil phase is pressed through the membrane pores to form the emulsion. The porous membrane is made by a phase separation process in the glass. The size of the pores formed can be tuned by the annealing time and temperature used in the manufacture of the glass membrane which determines the degree of phase separation in the glass phase, and thus the resulting pores.

Another manner of obtaining particles of a narrow polydispersity is to manufacture the particles by any technique, including those listed above, and then sieve the particles to obtain a particular size range. Sieving works well for those particles which are spherical or nearly spherical.

Examples of drugs that may be suitable for use in the method of this invention depending, of course, on the specific disease being treated, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, antimetabolic, angiogenic, cytoprotective, angiotensin converting enzyme (ACE) inhibiting, angiotensin II receptor antagonizing and/or cardioprotective drugs.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiogensin II receptor antagonists include, without limitation, irbesartan and losartan.

Other active agents that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides and ribozymes and retroviral vectors for use in gene therapy, antiviral drugs and diuretics.

Presently preferred drugs are halofuginone, ruboxistaurin, sirolimus, everolimus, zotarolimus, temsirolimus, pimecrolimus and biolimus.

Other polymers, biostable and/or biodegradable, may be included in the coatings and particles of the present invention along with the polymers of the present invention, that is the poly(ester-amide)s and poly(amide)s encompassed by the formula outlined above, and combinations thereof. Representative examples of polymers that may be used include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly (trimethylene carbonate), poly(ester-amide) polymers generally, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alpha-olefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose, ethylene vinyl alcohol copolymer (commonly known by the generic name EVOH or by the trade name EVAL™), poly(butyl methacrylate), poly(vinylidene fluoride-co-hexafluoropropene) (e.g., SOLEF 21508™, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol, and combinations thereof.

The particles and coatings of this invention may also includes additional components such as, but not limited to, wetting agents, lubricating agents, fillers, plasticizing agents, surfactants, diluents, mold release agents, agents which act as drug carriers or binders, anti-tack agents, anti-foaming agents, viscosity modifiers, anti-oxidants, adhesion promoters, coupling agents, potentially residual levels of solvents, and potentially any other agent which aids in, or is desirable in, the processing of the material, and/or is useful or desirable as a component of the final product.

The particles and coatings of the present invention can be used for local drug delivery. The particles can be injected either subcutaneously or locally into a particular tissue or organ. One non-limiting example of local delivery of a drug is the use of a drug-eluting stent (DES) to treat restenosis, a re-narrowing of a blood vessel after a procedure such as PCTA has been used to open a blocked or partially blocked artery.

EXAMPLES

The following examples are given to aid in understanding the invention, but it is to be understood that the invention is not limited to the particular materials or procedures of examples.

Example 1

Release Rate Testing of Coated Stents

All stents were cleaned by being sonicated in isopropyl alcohol, followed by an argon plasma treatment. No primer layer was applied to the stents. Coating layers of everolimus and poly(ester-amide) polymers of the general formula shown in FIG. 3 were applied to stainless steel stents of size 3.0×12 mm (Vision™). The specific substituents for the different polymers used in the coatings are illustrated in Table 1, and all $R_{b1}$, $R_{b1'}$, $R_{b2}$, and $R_{b2'}$ are —(CH$_2$)—(CH(CH$_3$)$_2$. These polymers are all poly(ester-amide) polymers. As described above, each $A_i$ has the chemical structure:

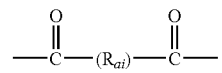

and each $B_j$ has the chemical structure

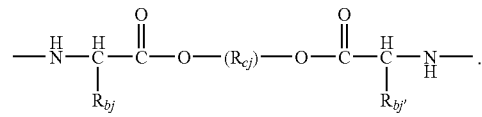

Figure 3:
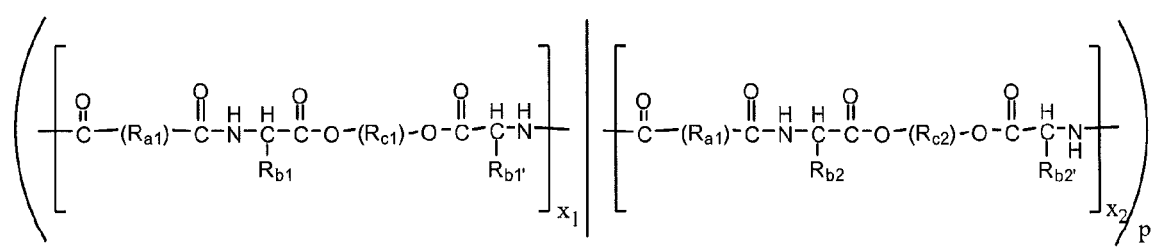
FIG. 3 is a depiction of the generic structure of one subgroup of polymers of the present invention.

Thus, the polymers in Table 1 are random copolymers of two constitutional units, $A_1$-$B_1$ and $A_1$-$B_2$, which are represented by the subscripts X1 and X2 in FIG. 3.

Application of a coating layer on the stents was accomplished by spraying the stents with a solution of everolimus (Novartis) and poly(ester-amide) at a 1:5 mass ratio in ethanol (absolute ethanol). The weight % polymer in solution was 2%. The objective drug loading for each stent was 56 µg for each of the 12 mm stents. The poly(ester-amide) polymer was manufactured by standard methods. The poly(ester-amide) polymer was purified and reprecipitated several times, and there were no detectable levels, or essentially no detectable levels, of residual reactants or catalysts. The poly(ester-amide) utilized had a weight-average molecular weight of about 140,000 Daltons relative to polystyrene standard using gel permeation chromatography with a refractive index detector.

TABLE 1

Polymers for Coatings

| | $R_{a1}$ | $R_{c1}$ | $R_{c2}$ | Molar Ratio $R_{c1}/R_{c2}$ | $s_1$ | $T_1$ | $t_2$ |
|---|---|---|---|---|---|---|---|
| 10 | —(CH$_2$)$_8$— | —(CH$_2$)$_6$— |  | 75:25 | 0.5 | 0.375 | 0.125 |
| 11 | —(CH$_2$)$_8$— | —(CH$_2$)$_6$— | 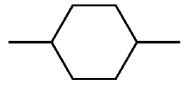 | 50:50 | 0.5 | 0.25 | 0.25 |

TABLE 1-continued

Polymers for Coatings

| | $R_{a1}$ | $R_{c1}$ | $R_{c2}$ | Molar Ratio $R_{c1}/R_{c2}$ | $s_1$ | $T_1$ | $t_2$ |
|---|---|---|---|---|---|---|---|
| 12 | —(CH$_2$)$_8$— | —(CH$_2$)$_6$— |  | 25:75 | 0.5 | 0.125 | 0.375 |
| 13 | —(CH$_2$)$_8$— | —(CH$_2$)$_6$— |  | 0:100 | 0.5 | 0 | 0.5 |
| 20 | —(CH$_2$)$_4$— | —(CH$_2$)$_6$— |  | 100:0 | 0.5 | 0.5 | 0 |
| 21 | —(CH$_2$)$_4$— | —(CH$_2$)$_6$— |  | 50:50 | 0.5 | 0.25 | 0.25 |
| 22 | —(CH$_2$)$_4$— | —(CH$_2$)$_6$— |  | 0:100 | 0.5 | 0 | 0.5 |
| 30 | —(CH$_2$)$_4$— | —(CH$_2$CH$_2$O)$_2$CH$_2$CH$_2$— |  | 100:0 | 0.5 | 0.5 | 0 |
| 31 | —(CH$_2$)$_8$— | —(CH$_2$CH$_2$O)$_2$CH$_2$CH$_2$— |  | 50:50 | 0.5 | 0.25 | 0.25 |
| 32 | —(CH$_2$)$_8$— | —(CH$_2$CH$_2$O)$_2$CH$_2$CH$_2$— |  | 25:75 | 0.5 | 0.125 | 0.375 |
| 33 | —(CH$_2$)$_8$— | —(CH$_2$CH$_2$O)$_2$CH$_2$CH$_2$— |  | 0:100 | 0.5 | 0 | 0.5 |

The spraying operation was carried out with a custom made spray coater equipped with a spray nozzle, a drying nozzle, and a means to rotate and translate the stent under the nozzles with the processing parameters outlined in Table 2. Subsequent to coating, all stents were baked in a forced air convection oven at 50° C. for 60 minutes. More than one pass under the spray nozzle was required to obtain the target weight of coating layer on the stent. The coating layer thickness was 3.0±1.5 μm. After heat treatment of the coating, the stents were crimped onto 3.0×12 mm Xience V catheters, and then sealed in Argon filled foil pouches. These stents were sterilized by electron beam sterilization by one pass through the electron beam at 25 KGy or by ethylene oxide.

TABLE 2

| Spray Processing Parameters for Coating | |
|---|---|
| Drug Layer | |
| Spray Head | |
| Spray nozzle to mandrel distance (mm) | 10 ± 5 |
| Solution flow rate | 2.5 ± 0.3 ml/mm |
| Atomization pressure (psi) | 15 ± 2.5 |
| Air Dry Heat Nozzle | |
| Drying nozzle temp (° C.) | 60 |
| Drying nozzle pressure (psi) | 20 ± 2 |
| Spray nozzle to mandrel dist (mm) | 12 ± 1 |
| Flow Rate and Coating Weight | |
| Target Flow Rate in μg/pass | 10 ± 2 |
| Target Weight (μg) | 336 |

Cumulative release of the everolimus over 3 days was determined using the United States Pharmacopeia type VII tester using porcine serum as the dissolution media at a temperature of 37° C. Everolimus that was released into solution was determined by HPLC. The glass transition temperature was measured by standard differential scanning calorimetry with a temperature ramp of 10° C./min utilizing nitrogen or argon atmosphere. Table 3 summarizes the results of the cumulative release rate testing and the glass transition temperatures.

TABLE 3

Cumulative Release Rate of Everolimus after 3 days for Polymer Coated Stents

| Polymer | Tg (° C.) | Cumulative Release after 3 days (%) |
|---|---|---|
| 10 | 31 | N/A |
| 11 | 49 | 20 |
| 12 | 59 | 7 |
| 13 | 83 | 7 |
| 20 | 36 | N/A |
| 21 | 45 | 71 |
| 22 | 83 | 7 |
| 30 | 21 | N/A |
| 31 | 29 | N/A |
| 32 | 56 | 20 |
| 33 | 83 | 7 |

Example 2

Figure 4:
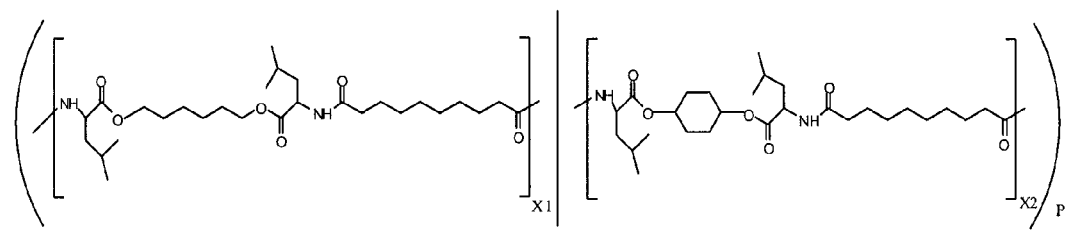
FIG. 4 is a depiction of the structure of one of the specific polymers of the present invention.

Preparation of ApoA1 Peptide Poly(Ester-Amide) (PEA) Polymer Microparticles Using the Water-in-Oil-in-Water (W1/O/W2) Double Emulsion Technique PEA particles containing peptide ApoA1 (molecular weight approximately 2300 Da) were prepared using the water in oil in water double emulsion solvent evaporation technique. The PEA polymer used was a random copolymer of the structure illustrated in FIG. 4 in which there was a 1:1 ratio of the two constitutional units (represented by x1 and x2 subscripts) shown. The weight average molecular weight of the polymer used is approximately 50-70 kDa.

A solution of PVA (polyvinyl alcohol) in DI (deionized) water (150 mL) (water continuous phase) was prepared. A second solution of PVA in water (750 mL) was prepared and to this was added the ApoA1 (77 mg) (W1). Then a solution of PEA (180 mg) in methylene chloride (4 mL) (O) was added to the (W1) solution and the mixture was sonicated in an ultra sonicator for one minute to form a W1/O emulsion. A solution of PVA in DI water (8 mL) (W2) was then added to the (W1/O) emulsion followed again by sonication to give a second emulsion (W1/O/W2), which was immediately poured into the continuous water phase, stirred at 500 rpm for 5 minutes and 300 rpm for 3 hours. The microparticles which formed were separated by centrifugation. The supernatant liquid was collected and discarded leaving precipitated particles as pellets. The particle pellets were washed twice with water and then suspended in water followed by lyophilization to provide the particles in powder form. Encapsulation efficiency, that is the percent of the added peptide that ended up in the particles, was about 99%.

Example 3

In-Vitro Cumulative Release Profile

Figure 5:
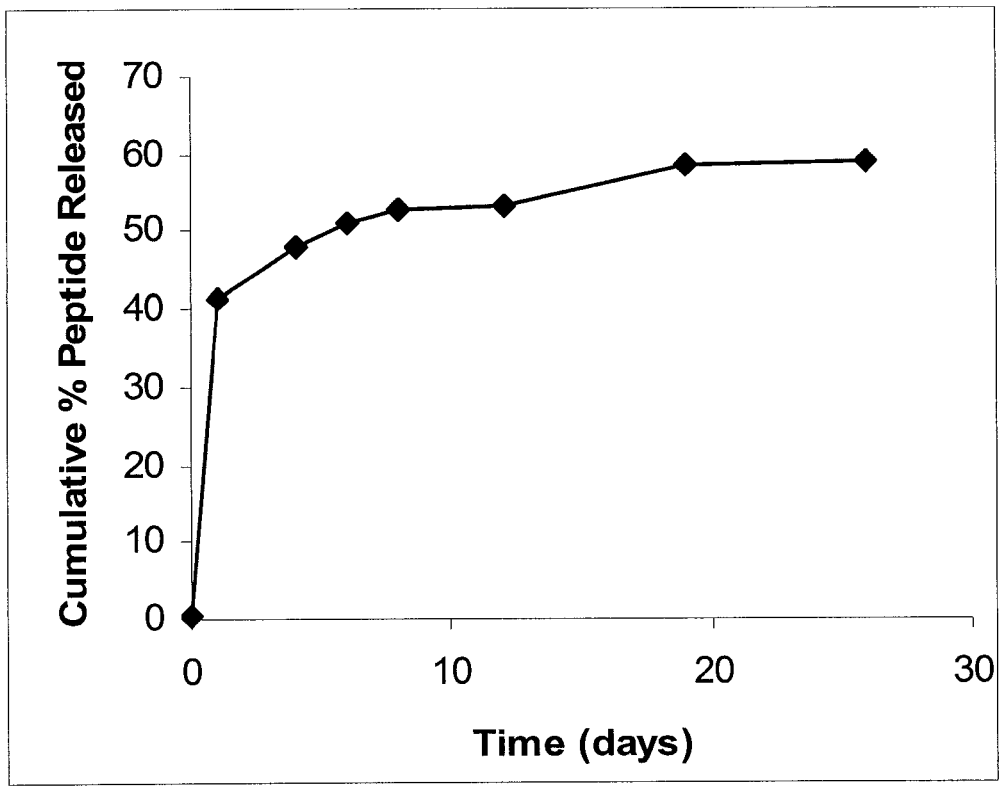
FIG. 5 is a depiction of the cumulative release profile of an exemplary embodiment of the particles of the present invention.

For the particles manufactured in example 2, an in vitro release study was performed. Thus, 10 mg of dried, peptide loaded PEA microparticles were weighed, put into a 1.7 ml Eppendorf microcentrifuge tube and followed by adding 1 ml of PBS (phosphate buffer solution, pH about neutral) buffer with 0.5% TRITON 80™ (a surfactant). Every other day, the tube was centrifuged down and the supernatant solution removed. Then, fresh PBS buffer with 0.5% Triton 80 was added to the tube. The concentration of ApoA1 in the supernatant was measured by HPLC. For each time point, 3 tubes will be used. FIG. 5 illustrates the release profile.

Example 4

Preparation of Dexamethasone Loaded PEA Microparticles Using Spray Drying

A solution of the poly(ester-amide) of example 2 (180 mg) and dexamethasone (20 mg) in acetone (10 mL) (O) is prepared. This organic solution is sprayed from a Bucchi Mini Spray dryer 290 and dried under the condition of inlet temperature 65° C., amplitude 100%, and a pump rate of 20% of the maximum. Spherical dexamethasone loaded PEA microparticles powder is collected from the collecting flask.

Example 5

Figure 6:
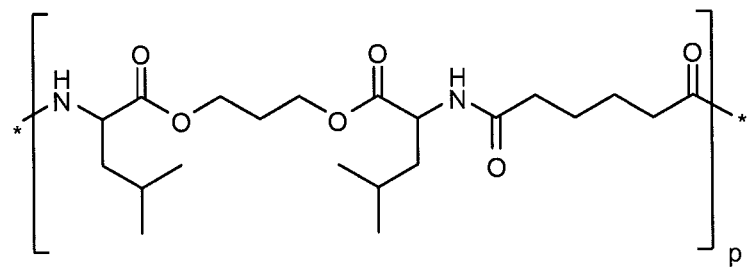
FIG. 6 is a depiction of the structure of one of the specific polymers of the present invention.

Preparation of Peptide Pea Microparticles Using the Water-in-Oil-in-Water (W1/O/W2) Double Emulsion Technique Drug delivery particles using a polymer of the present invention and containing a peptide were manufactured utilizing the water in oil in water double emulsion solvent evaporation technique. The polymer used was a poly(ester-amide) (PEA) polymer of the structure illustrated in FIG. 6. The procedure used was the same described in Example 2. Encapsulation efficiency, that is the percent of the added drug that ends up in the particles, was greater than or equal to 85%.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

What is claimed:
1. A polymer of the formula:

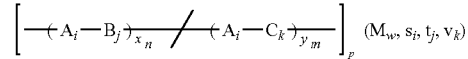

wherein:
i is an integer that varies from 1 to an integer less than or equal to 10 which represents the $i^{th}$ type of $A_i$ group;
j is an integer that varies from 1 to an integer less than or equal to 10 which represents the $j^{th}$ type of $B_j$ group;
k is an integer that varies from 0 to an integer less than or equal to 15 which represents the $k^{th}$ type of $C_k$ group;
each $x_n$ is an integer from 1 to 100, inclusive, which represents the number of $A_i$-$B_j$;
each $y_m$ is an integer from 0 to 150, inclusive, which represents the number of $A_i$-$C_k$;
p is an integer from 2 to about 4500, which represents the average number of constitutional units in a polymer chain, wherein a constitutional unit is a repeating unit in the polymer chain;
$M_w$ is from about 10,000 to about 1,000,000 Da, which represents the weight average molecular weight of the polymer;
$s_i$ is a number from 0 to 0.5, inclusive, which represents the average mole fraction of each of the $A_i$;

$t_j$ is a number from 0 to 0.5, inclusive, which represents the average mole fraction of each of the $B_j$;
$v_k$ is a number from 0 to 0.5, inclusive, which represents the average mole fraction of each of the $C_k$;
with the proviso that $\Sigma_i s_i + \Sigma_j t_j + \Sigma_k v_k = 1.0$;

$\Sigma_i s_i = \Sigma_j t_j + \Sigma_k v_k = 0.5$;

$\Sigma_i s_i > 0$;

$\Sigma_j t_j > 0$;

each $A_i$ has the chemical structure:

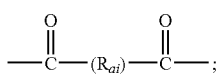

each $B_j$ has the chemical structure

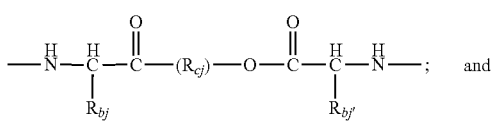

each $C_k$ has the chemical structure:

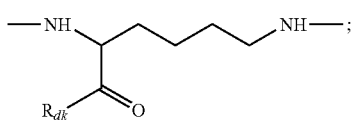

wherein:
each $R_{bj}$, and $R_{bj'}$ are independently selected from the group consisting of hydrogen and (1C-4C)alkyl, wherein: the alkyl group is optionally substituted with a moiety selected from the group consisting of —OH, —SH, —SeH, —C(O)OH, —NHC(NH)NH$_2$,

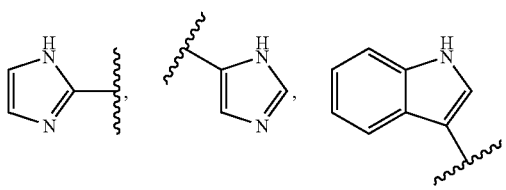

phenyl and

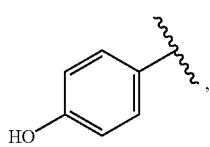

or one or more of $R_{bj}$ and $R_{bj'}$ may form a bridge between the carbon to which it is attached and the adjacent nitrogen, the bridge comprising —CH$_2$CH$_2$CH$_2$—;

each $R_{ai}$ is independently selected from the group consisting of (1C-12C)alkyl, (2C-12C)alkenyl, (3C-8C)cycloalkyl, —(CH$_2$CH$_2$O)$_q$CH$_2$CH$_2$— wherein q is an integer from 1 to 10, inclusive, and

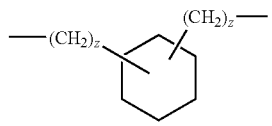

where z is 0, 1, or 2;
each $R_{cj}$ is independently selected from the group consisting of (1C-12C)alkyl, (2C-12C)alkenyl, (3C-8C)cycloalkyl, —(CH$_2$CH$_2$O)$_q$CH$_2$CH$_2$— wherein q is an integer from 1 to 10, inclusive, and

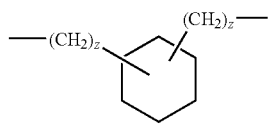

where z is 1 or 2, wherein:
at least one $R_{ai}$ is selected from the group consisting of

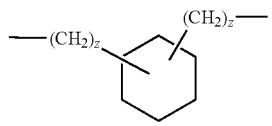

where z is 0, 1, or 2, or at least one $R_{cj}$ is selected from the group consisting of

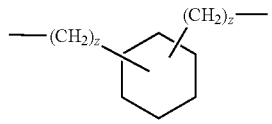

where z is 1 or 2, and allows for tuning of the miscibility and release rate characteristics of the polymer;
$R_{dk}$ is selected from the group consisting of a drug, a peptide, a straight or branched chain polymer, a brush polymer, a paramagnetic moiety, a contrast agent, —H, —OH, —O(1C-20C)alkyl, —O(2C-20C)alkenyl and —O(CH$_2$CH$_2$O)$_w$CH$_2$CH$_2$OR$_{ek}$, wherein:
w is an integer from 1 to 600, inclusive;
$R_{ek}$ is selected from the group consisting of hydrogen, —C(O)CH=CH$_2$ and —C(O)C(CH$_3$)=CH$_2$; and,
each $R_{ai}$ corresponds to the $i^{th}$ $A_i$ group, each $R_{bj}$, $R_{bj'}$, and $R_{cj}$ corresponds to the $j^{th}$ $B_j$ group, and each $R_{dk}$ and optionally $R_{ek}$ correspond to the $k^{th}$ $C_k$ group.

2. The polymer of claim 1, wherein for each $B_j$, $R_{bj}$, and $R_{bj'}$ are the same.

3. The polymer of claim 2, wherein for each $R_{bj}$, and $R_{bj'}$ are selected from the group consisting of —CH$_3$, —CH$_2$CH(CH$_3$)$_2$, and

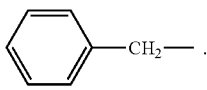

4. The polymer of claim 1, wherein
i is 1 or varies from 1 to 2, j is 2, and k=0;
each of $R_{a1}$ and $R_{a2}$ are independently selected from the group consisting of —$(CH_2)_6$—, —$(CH_2)_7$—, —$(CH_2)_8$—, —$(CH_2)_9$—, and —$(CH_2)_{10}$—;
each of $R_{b1}$ $R_{b1'}$, $R_{b2}$ and $R_{b2'}$ are the same, and are selected from the group consisting of —$(CH_2)$—$(CH(CH_3)_2)$ and —$CH_3$;
$R_{c1}$ is selected from the group consisting of —$(CH_2)_4$—, —$(CH_2)_5$—, —$(CH_2)_6$—, —$(CH_2)_7$—, and —$(CH_2)_8$—; and
$R_{c2}$ is selected from the group consisting of

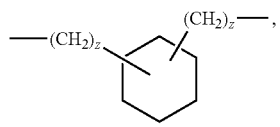

where z is 1 or 2.

5. The polymer of claim 1, wherein
i=1, j is 2, and k=0;
$R_{a1}$ is —$(CH_2)_8$—;
$R_{b1}$, $R_{b1'}$, $R_{b2}$ and $R_{b2'}$ are —$(CH_2)$—$(CH(CH_3)_2)$;
$R_{c1}$ is —$(CH_2CH_2O)_2CH_2CH_2$—;
$R_{c2}$ is selected from the group consisting of

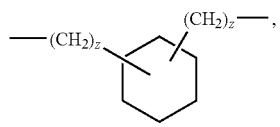

where z is 1 or 2;
$s_1$=0.5; and
$t_1$ is between 0.10 and 0.15, inclusive.

6. An implantable medical device, comprising:
a device body; and,
at least one coating layer comprising a polymer of claim 1.

7. An implantable medical device, comprising:
a device body; and,
at least one coating layer comprising a polymer of claim 2.

8. An implantable medical device, comprising:
a device body; and,
at least one coating layer comprising a polymer of claim 3.

9. An implantable medical device, comprising:
a device body; and,
at least one coating layer comprising a polymer of claim 4.

10. The device of claim 6, wherein the implantable medical device is a stent.

11. The device of claim 10, wherein the at least one coating layer further comprises a drug.

12. The device of claim 11, wherein the drug is selected from the group consisting of sirolimus (rapamycin), umirolimus, deforolimus, AP23573 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin, 40-O-[2-(2-hydroxy)ethoxy] ethyl-rapamycin, 40-O-tetrazole-rapamycin, 40-O-tetrazolylrapamycin, 40-epi-(N1-tetrazole)-rapamycin, and combinations thereof.

13. The device of claim 9, wherein the implantable medical device is a stent.

14. The device of claim 13, wherein the at least one coating layer further comprises a drug.

15. The device of claim 14, wherein the drug is selected from the group consisting of sirolimus (rapamycin), umirolimus, deforolimus, AP23573 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin, 40-O-[2-(2-hydroxy)ethoxy] ethyl-rapamycin, 40-O-tetrazole-rapamycin, 40-O-tetrazolylrapamycin, 40-epi-(N1-tetrazole)-rapamycin, and combinations thereof.

* * * * *

UNITED STATES PATENT AND TRADEMARK OFFICE
CERTIFICATE OF CORRECTION

| | |
|---|---|
| PATENT NO. | : 8,765,162 B2 |
| APPLICATION NO. | : 12/165173 |
| DATED | : July 1, 2014 |
| INVENTOR(S) | : Ngo et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this
Twenty-second Day of September, 2015

Michelle K. Lee
*Director of the United States Patent and Trademark Office*